US012559520B2

(12) United States Patent
El Menyawi et al.

(10) Patent No.: US 12,559,520 B2
(45) Date of Patent: *Feb. 24, 2026

(54) METHOD FOR EXTRACTING A PROTEIN FROM A PRECIPITATE AND METHOD FOR PRECIPITATING IMPURITIES

(71) Applicant: CSL BEHRING AG, Bern (CH)

(72) Inventors: Ibrahim El Menyawi, Bern (CH); Marcus Von Nordheim, Bern (CH)

(73) Assignee: CSL Behring AG, Bern (CH)

( * ) Notice: Subject to any disclaimer, the term of this patent is extended or adjusted under 35 U.S.C. 154(b) by 951 days.

This patent is subject to a terminal disclaimer.

(21) Appl. No.: 17/778,394

(22) PCT Filed: Nov. 20, 2020

(86) PCT No.: PCT/EP2020/082806
§ 371 (c)(1),
(2) Date: May 19, 2022

(87) PCT Pub. No.: WO2021/099529
PCT Pub. Date: May 27, 2021

(65) Prior Publication Data
US 2023/0002444 A1     Jan. 5, 2023

(30) Foreign Application Priority Data
Nov. 20, 2019     (AU) ................................ 2019904386

(51) Int. Cl.
*C07K 1/36*     (2006.01)
*C07K 1/32*     (2006.01)
*C07K 1/34*     (2006.01)

(52) U.S. Cl.
CPC .................. *C07K 1/36* (2013.01); *C07K 1/32* (2013.01); *C07K 1/34* (2013.01)

(58) Field of Classification Search
None
See application file for complete search history.

(56) References Cited

U.S. PATENT DOCUMENTS

| | | | |
|---|---|---|---|
| 3,301,842 A | 1/1967 | Schultze et al. | |
| 11,312,746 B2 * | 4/2022 | El Menyawi ............ | C07K 1/34 |
| 2004/0167320 A1 | 8/2004 | Couto et al. | |
| 2005/0053707 A1 | 3/2005 | Kopf et al. | |
| 2011/0130545 A1 | 6/2011 | Hensgens et al. | |

FOREIGN PATENT DOCUMENTS

| | | |
|---|---|---|
| CN | 102970975 A | 3/2013 |
| CN | 104245730 A | 12/2014 |
| CN | 108939922 A | 12/2018 |
| CN | 112074528 A1 | 12/2020 |
| EP | 1 247 818 A2 | 10/2002 |
| EP | 0 893 450 | 5/2004 |

| | | | | | |
|---|---|---|---|---|---|
| EP | 2583744 A1 * | 4/2013 | .......... | B01D 61/147 |
| JP | H03-271234 A | 12/1991 | | |
| WO | WO-00/48703 A1 | 8/2000 | | |
| WO | WO-2005/007269 A1 | 1/2005 | | |
| WO | WO-2019/219890 A1 | 11/2019 | | |

OTHER PUBLICATIONS

Levesley et al. The effect of high frequency backflushing on the microfiltration of yeast homogenate suspensions for the recovery of soluble proteins, Journal of Membrane Science, vol. 158, Issues 1-2, https://doi.org/10.1016/S0376-7388(99)00031-9. (Year: 1999).*
Espina et al. Fractionation of pasteurized skim milk proteins by dynamic filtration, Food Research International, vol. 43, Issue 5, 2010, https://doi.org/10.1016/j.foodres.2010.03.023. (Year: 2010).*
Martinez et al. Precipitation as an Enabling Technology for the Intensification of Biopharmaceutical Manufacture. Trends Biotechnol. Mar. 2019;37(3):237-241. doi: 10.1016/j.tibtech.2018.09.001. Epub Oct. 10, 2018. PMID: 30316558. (Year: 2019).*
Hitachi Koki Co., Ltd; "Suppressing clogging due to nano-sized particle! Utilization dictionary of rotational cross-flow filter"; http://www.takayamarika.co.jp/wp/wp-content/uploads/2018/05/ad6fdcdac72229db89442660151080c7.pdf; Feb. 2018; 9 pages.
Japanese Patent Office; Notice of Reasons for Rejection (English translation); Japanese Patent Application No. 2022-529291; Oct. 29, 2024; 6 pages.
Cohn et.al. "A System for the Separation of the Components of Human Blood: Quantitative Procedures for the Separation of the Protein Components of Human Plasma" (1950) J. Am; Chem. Soc., 72, 465-474.
Deutsch et.al. "Biophysical Studies of Blood Plasma Proteins, III. Recovery of Y-Globulin from Human Blood Protein Mixtures," J. Biol. Chem. 164, 109-118 (1946).
Nitschmann et al., Helv. Chim. Acta 37, 866-873 (1954).
L. Castilho et al. "An integrated process for mammalian cell perfusion cultivation and product purification using a dynamic filter" Biotechnology Progress, American Chemical Society, vol. 18, No. 4, Jul. 1, 2002 (Jul. 1, 2002), pp. 776-781, XP009138350, ISSN: 8756-7938, DOI: 10.1021/BP0255154.
Nitschmann and Kistler "Large Scale Production of Human Plasma Fractions" Vox Sang. 7, 414-424 (1962).
Oncley et al., "The Separation of the Antibodies, Isoagglutinins, Prothrombin, Plasminogen and B_1-Lipoprotein into Subfractions of Human Plasma^1a,b" (1949) J. Am. Chem. Soc. 71, 541-550.
Schultze H.E., Heremans J.F.; vol. I: Nature and Metabolism of Extracellular Proteins 1966, Elsevier Publishing Company; p. 236-317.
Wu Zhiwei et al.; "Research on the Caprylic Acid Separation Process for Intravenous Human Immunoglobulin"; The World Clinical Medicine; Aug. 2015; pp. 273-275.
Hao, Yu-lee et al.; "A Simplified Method for the Preparation of Immune-Serum Globulin"; Vox Sang, vol. 40, No. 4; Apr. 1981; pp. 278-285.

* cited by examiner

*Primary Examiner* — Daniel E Kolker
*Assistant Examiner* — Julia A Rossi
(74) *Attorney, Agent, or Firm* — Foley & Lardner LLP

(57) ABSTRACT
The present invention relates to a method and system for extracting proteins from precipitates, particularly recombinant and/or plasma derived proteins including immunoglobulins (Ig) such as immunoglobulin G (IgG).

20 Claims, 2 Drawing Sheets

FIGURE 2

METHOD FOR EXTRACTING A PROTEIN FROM A PRECIPITATE AND METHOD FOR PRECIPITATING IMPURITIES

CROSS-REFERENCE TO RELATED APPLICATIONS

The present application is the U.S. National Stage of International Application No. PCT/EP2020/082806, filed Nov. 20, 2020, and claims priority to Australian Patent Application No. 2019904386, filed Nov. 20, 2019.

FIELD OF THE INVENTION

The present invention relates to a method and system for extracting proteins from precipitates, particularly recombinant and/or plasma derived proteins including immunoglobulins (Ig) such as immunoglobulin G (IgG).

RELATED APPLICATION

This application claims priority from Australian provisional application AU2019904386, the contents of which are hereby incorporated by reference in their entirety.

BACKGROUND OF THE INVENTION

The demand for purified proteins such as specific antibodies has increased considerably. Such purified proteins can be used for therapeutic and/or diagnostic purposes.

Human blood plasma has been industrially utilized for decades for the production of widely established and accepted plasma-protein products such as human albumin (HSA), immunoglobulin (IgG), clotting factor concentrates (clotting Factor VIII, clotting Factor IX, prothrombin complex etc.) and inhibitors (antithrombin, C1-inhibitor etc.). In the course of the development of such plasma-derived drugs, plasma fractionation methods have been established, leading to intermediate products enriched in certain protein fractions, which then serve as the starting composition for plasma-protein product/s. Typical processes are reviewed in e.g. Molecular Biology of Human Proteins (Schultze H. E., Heremans J. F.; Volume I: Nature and Metabolism of Extracellular Proteins 1966, Elsevier Publishing Company; p. 236-317). These kinds of separation technologies allow for the production of several therapeutic plasma-protein products from the same plasma donor pool. This is economically advantageous over producing only one plasma-protein product from one donor pool, and has therefore been adopted as the industrial standard in blood plasma fractionation.

One example of this type of fractionation process, cold ethanol fractionation of plasma, was pioneered by E. J Cohn and his team during World War II, primarily for the purification of albumin (Cohn E J, et al. 1946, J. Am. Chem. Soc. 62: 459-475). The Cohn fractionation process involves increasing the ethanol concentration in stages, from 0% to 40%, while lowering the pH from neutral (pH 7) to about 4.8, resulting in the precipitation of albumin. Whilst Cohn fractionation has evolved over the past 70 years or so, most commercial plasma fractionation processes are based on the original process or a variation thereof (e.g. Kistler/Nitschmann), exploiting differences in pH, ionic strength, solvent polarity and alcohol concentration to separate plasma into a series of major precipitated protein fractions (such as Fractions Ito V in Cohn).

Variations to the Cohn Fractionation process have been developed with the aim of improving polyvalent IgG recovery. For example Oncley and co-workers used Cohn Fractions II+III as a starting material with different combinations of cold ethanol, pH, temperature and protein concentration to those described by Cohn, to produce an active immune globulin serum fraction (Oncley et al., (1949) J. Am. Chem. Soc. 71, 541-550). Today, the Oncley method is the classic method used for production of polyvalent IgG. Nevertheless, it is known that approximately 5% of gamma-globulins (antibody-rich portion) is co-precipitated with Fraction I and about 15% of the total gamma-globulin present in plasma is lost by the Fraction II+III step (See Table III, Cohn E J, et al. 1946, J. Am. Chem. Soc. 62: 459-475). The Kistler/Nitschmann method aimed to improve IgG recovery by reducing the ethanol content of some of the precipitation steps (Precipitation B vs Fraction III). The increased yield, however, is at the expense of the purity (Kistler & Nitschmann, (1962) Vox Sang. 7, 414-424).

Initially, immunoglobulin G (IgG) preparations derived from these fractionation processes were successfully used for the prophylaxis and treatment of various infectious diseases. However, as ethanol fractionation is a relatively crude process the IgG products contained impurities and aggregates to an extent that they could only be administered intramuscularly. Since that time additional improvements in the purification processes have led to IgG preparations suitable for intravenous (called IVIg) and subcutaneous (called SCIg) administration.

It has been estimated that approximately 30 million liters of plasma were processed worldwide in 2010, providing a range of therapeutic products including about 500 tonnes of albumin and 100 tonnes of IVIg. The IVIg market accounts for about 40-50% of the entire plasma fractionation market (P. Robert, Worldwide supply and demand of plasma and plasma derived medicines (2011) J. Blood and Cancer, 3, 111-120). Thus, with demands for IVIg remaining strong (along with increasing demands for SCIg) there remains a need to improve immunoglobulin recoveries from plasma and related fractions. Preferably, this must be achieved in a way that ensures the recovery of other plasma derived therapeutic proteins is not adversely affected.

From a commercial perspective, the initial fractionation processes are critical to the overall production time and costs associated with the production of a therapeutic protein, particularly plasma derived proteins, since the subsequent purification steps will depend on the yield and purity of the protein(s) of interest within these initial fractions. Whilst several variations of the cold ethanol fractionation process have been developed for plasma derived protein in order to improve protein yield at lower operating costs, higher protein yields are typically associated with lower purity.

There is a need for an improved method and system for the industrial scale production of proteins such as immunoglobulins from immunoglobulin-comprising precipitate material, for example derived from plasma or serum, which have to meet stringent safety standards. The currently used downstream technologies are relatively expensive and their yield is not optimal.

Therefore, there is a crucial need to develop more efficient and economic methods for the extraction and purification of proteins such as immunoglobulins from protein containing suspensions.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

According to a first aspect of the invention, there is provided a method for extracting a protein of interest from a precipitate, comprising:

a) mixing the precipitate with a liquid in a first tank to form a first suspension having a first dilution factor;

b) feeding the first suspension into a first filtration unit comprising a dynamic filter element adapted to produce a first retentate depleted for the protein of interest and a first permeate enriched with the protein of interest;

c) diluting the first suspension in the first tank by adding liquid to a second dilution factor, optionally by streaming the first retentate into the first tank;

d) recovering the first permeate enriched with the protein of interest in a second tank;

e) precipitating one or more impurities in the first permeate enriched with the protein of interest to produce a second suspension; and f) removing the precipitated impurities from the second suspension to produce a solution containing the protein of interest.

In any embodiment of the above aspect of the invention, there is provided a step of concentrating the first permeate enriched with the protein of interest prior to the step of precipitating the one or more impurities in the first permeate.

In any embodiment of the first aspect of the invention, removing the precipitated impurities from the second suspension to produce a solution containing the protein of interest may comprise:

a) feeding the second suspension into a second filtration unit comprising a dynamic filter element adapted to produce a second retentate containing the one or more precipitated impurities and a second permeate enriched with the protein of interest;

b) optionally streaming the second retentate into the tank comprising the second suspension;

c) recovering the second permeate enriched with the protein of interest in a further tank.

Preferably, removing the precipitated impurities from the second suspension to produce a solution containing the protein of interest further comprises:

a) subjecting the second permeate in the further tank to a continuous concentration process in a third filtration unit comprising a cross flow filter element, thereby producing a third retentate enriched with the protein of interest and a third permeate depleted of the protein of interest;

b) optionally diluting the suspension in the tank comprising the second suspension by streaming the third permeate to the tank comprising the second suspension, thereby diluting the suspension to a third dilution factor; and c) either returning the third retentate enriched with the protein of interest to the third tank and/or collecting the third retentate enriched with the protein of interest.

According to a second aspect of the invention, there is provided a method for extracting a protein of interest from a precipitate, comprising:

a) mixing the precipitate with a liquid in a first tank to form a first suspension having a first dilution factor;

b) feeding the first suspension into a first filtration unit comprising a dynamic filter element adapted to produce a first retentate depleted for the protein of interest and a first permeate enriched with the protein of interest;

c) diluting the first suspension in the first tank by adding liquid to a second dilution factor, optionally by streaming the first retentate into the first tank;

d) recovering the first permeate enriched with the protein of interest in a second tank;

d1) subjecting the first permeate in the second tank to a continuous concentration process in a second filtration unit comprising a cross flow filter element, adapted to produce a second retentate, enriched with the protein of interest and a second permeate, depleted of the protein of interest;

d2) optionally diluting the first suspension in the first tank by streaming the second permeate to the first tank, thereby diluting the suspension to the second dilution factor; and d3) either returning the second retentate enriched with the protein of interest to the second tank and/or collecting the second retentate enriched with the protein of interest;

e) precipitating one or more impurities from the second retentate enriched with the protein of interest to produce a second suspension; and f) removing the precipitated impurities from the second suspension to produce a solution containing the protein of interest.

In any embodiment of the second aspect of the invention, removing the precipitated impurities from the second suspension to produce a solution containing the protein of interest may comprise:

d) feeding the second suspension into a third filtration unit comprising a dynamic filter element adapted to produce a third retentate containing the one or more precipitated impurities and a third permeate enriched with the protein of interest;

e) optionally streaming the third retentate into the tank comprising the second suspension to a third dilution factor;

f) optionally recovering the third permeate enriched with the protein of interest in a further tank.

Preferably, removing the precipitated impurities from the second suspension to produce a solution containing the protein of interest further comprises:

d) subjecting the third permeate in the further tank to a continuous concentration process in a fourth filtration unit comprising a cross flow filter element, thereby producing a fourth retentate enriched with the protein of interest and a fourth permeate depleted of the protein of interest;

e) optionally diluting the suspension in the tank comprising the second suspension by streaming the fourth permeate to the tank comprising the second suspension, thereby diluting the suspension to the third dilution factor; and f) either returning the fourth retentate enriched with the protein of interest to the further tank and/or collecting the fourth retentate enriched with the protein of interest.

In any embodiment of the first or second aspects of the invention, precipitating the one or more impurities in step e) (e.g., precipitating impurities from the first permeate according to the first aspect of the invention, or from the second retentate of the second aspect of the invention) may be by altering the solvation potential of the solvent, more specifically, by lowering the solubility of the one or more impurities by addition of a reagent and/or modulating the conditions (e.g. like pH or conductivity).

In any embodiment the first or second aspects of the invention, the reagent for precipitating the one or more impurities from the first permeate is an ionisable organic additive, for example a fatty acid. Preferably, the fatty acid that comprises a general structural formula of $CH_3(CH_2)_n$ COOH. Preferably, the fatty acid is a C 4 to C 10 carboxylic acid. The fatty acid may be saturated or unsaturated. More preferably, the fatty acid comprises enanthic (heptanoic) acid, caprylic (octanoic) acid, octenoic acid, pelargonic (nonanoic) acid, nonenoic acid, or capric (decanoic) acid. Most preferably, the fatty acid is caprylic (octanoic) acid. Also contemplated as the reagent is a salt or ester of any fatty acid described herein, e.g. caprylate.

In any embodiment, the amount of fatty acid, preferably caprylic (octanoic) acid, is about 0.1 g/g total protein, about 0.5 g/g total protein, about 0.75 g/g total protein, about 1 g/g total protein, about 1.5 g/g total protein, about 2.0 g/g total protein, about 2.5 g/g total protein, about 3.0 g/g total protein, about 3.5 g/g total protein, or about 4.0 g/g total protein. Preferably, the amount of fatty acid, preferably caprylic (octanoic) acid, is about 0.275 g/g total protein, about 0.280 g/g total protein, about 0.285 g/g total protein, about 0.290 g/g total protein, about 0.300 g/g total protein, or about 0.325 g/g total protein.

In any embodiment, the amount of fatty acid, preferably caprylic (octanoic) acid, is 0.1 g/g total protein, 0.5 g/g total protein, 0.75 g/g total protein, 1.0 g/g total protein, 1.5 g/g total protein, 2.0 g/g total protein, 2.5 g/g total protein, 3.0 g/g total protein, 3.5 g/g total protein, or 4.0 g/g total protein. Preferably, the amount of fatty acid, preferably caprylic (octanoic) acid, is 0.275 g/g total protein, 0.280 g/g total protein, 0.285 g/g total protein, 0.290 g/g total protein, 0.300 g/g total protein, or 0.325 g/g total protein.

In any embodiment of the first or second aspects of the invention, the reagent for precipitating the one or more impurities from the first permeate is a nonionic organic polymer. The non-ionic organic polymer may be polyethylene glycol (PEG), polypropylene glycol, polyvinylpyrrolidone, dextran, cellulose, or other polymers.

In any embodiment of the first or second aspects of the invention, precipitating the one or more impurities in step e. may be performed using sequential precipitation with different amounts of a precipitation reagent.

Typically, the precipitate comprising the protein of interest is an insoluble solid that comprises the protein of interest. Often it is in the form of a pellet or a paste. Sometimes the precipitate can emerge as a suspension. The solid portion may then be collected by for example filtration and/or centrifugation. Alternatively, such a suspension may be added directly to the first tank to form the first dilution factor. Another option is to add the suspension to the first tank and then add liquid to the first tank to form the first dilution factor. Thus in a particular embodiment the precipitate comprising the protein of interest is in the form of a suspension when added to the first tank.

In any aspect of the present invention, the precipitate comprising the protein of interest is an intermediate product of an alcohol fractionation process, preferably of blood plasma, more preferably of human blood plasma. In preferred embodiments the precipitate is obtained from a human plasma starting material. Even more preferably the precipitate is obtained from 2500 L to 6000 L of a human plasma starting material.

In any aspect of the present invention, the precipitate comprising the protein of interest is a plasma fraction (intermediate). In particular embodiments the fraction is a Cohn Fraction. In a preferred embodiment the plasma fraction is selected from the group consisting of Cohn Fraction I (Fr I), Cohn Fraction II+III (Fr II+III), Cohn Fraction I+II+III (Fr I+II+III), Cohn Fraction II (Fr II), Cohn Fraction III (Fr III), Cohn Fraction IV (Fr IV), Cohn Fraction V (Fr V), Kistler/Nitschmann Precipitate A (KN A), Kistler/Nitschmann Precipitate B (KN B), Kistler/Nitschmann Precipitate C (KN C). In a particularly preferred embodiment the plasma fraction is selected from the group consisting of Cohn Fraction I (Fr I), Cohn Fraction II+III (Fr II+III), Cohn Fraction I+II+III (Fr I+II+III), or Kistler/Nitschmann Precipitate A (KN A). The plasma fraction may be a combination of different fractions. For example, the plasma fraction may be a combination of KN A and one or more of Fr 1, Fr II+III and Fr I+II+III.

The methods according to an aspect of the invention are suitable for extracting a protein of interest from other protein-containing solids. Examples include lyophilisates and crystalized solid forms comprising the protein of interest.

In any aspect of the present invention, the protein-comprising precipitate is obtained from a culture supernatant or a fermentation starting material. In some embodiments the starting material is milk or whey-containing composition comprising the protein of interest. In other embodiments the starting material is not milk.

In any aspect of the present invention, the protein of interest is an immunoglobulin, preferably human immunoglobulin G (IgG) such as immunoglobulin G from human plasma or a recombinantly produced immunoglobulin G.

In any aspect of the present invention, the protein of interest is albumin, preferably human albumin (HSA).

In any aspect of the present invention, the first suspension is produced by mixing the protein-comprising precipitate with a liquid such as a buffer or water, thereby providing the starting composition with the first dilution factor. When the protein-comprising precipitate is almost solid (e.g. very thick paste, pellet or etc.), addition of a liquid to the protein-comprising precipitate allows a suspension to be formed as the starting composition.

The first suspension having a first dilution factor of step a) is a mixture in which solute-like particles, sometimes herein referred to as solids, are present in the solution. The size of the particles can vary and includes larger particles that will eventually settle if the solution is not mixed or smaller sized particles that do not settle (i.e. in the form of a colloid).

The first dilution factor can sometimes be referred to as percent solids by weight (% w/v). This is defined as the weight of dry solids in a given volume of the suspension, divided by the total weight of that volume of the suspension, multiplied by 100. In particular embodiments the percent solids per weight of the suspension of step a) is at least 5% (i.e. a first dilution factor of about 1:20), or at least 7.5% or at least 10%, or at least 12.5%, or at least 15%, or at least 17.5%, or at least 20% or at least 22.5% or at least 25% or at least 27.5%, or at least 30%, or at least 35%, or at least 40%, or at least 50%. In some embodiments the percent solids per weight of the suspension of step a) is from 10% to 30%. In some embodiments the percent solids per weight of the suspension of step a) is from 15% to 25%. In preferred embodiments the percent solids per weight of the suspension of step a) is from 17.5% to 22.5%. In a particular embodiment the percent solids per weight of the suspension of step a) is 20%.

In any aspect of the present invention, the first dilution factor is at least 3 (1:3; parts precipitate:total), preferably between 1 to 10, preferably between 3 to 9, preferably between 3 to 5, preferably about 3, 5, 6, 7, 9 or 10. For example, when the protein-comprising precipitate is a pellet or a paste, and in particular a very thick paste (with very high viscosity), a liquid is required to suspend the paste or the pellet.

For example, when the first dilution factor is 3 (1:3; 1 part of the protein-comprising precipitate:total), this equates to a dilution ratio of 1:2 (1 unit volume of solute (the material to be diluted) with 2 unit volumes of the diluent to give 3 total units of total volume).

In any aspect of the present invention, the first dilution factor (protein-comprising precipitate:total) in the first tank is at least 40, or at least 30, or at least 20, or at least 17.5, or at least 15, or at least 12.5, or at least 10, or at least 9, or at least 8, or at least 7, or at least 6, or at least 5.5, or at least 5, or at least 4.5, or at least 4, or at least 3.5, or at least 3, or at least 2.5, or at least 2, or at least 1.5, or at least 1.25. Preferably the first dilution factor (protein-comprising precipitate:total) in the first tank is at least 4.

In some embodiments the first dilution factor (protein-comprising precipitate:total) in the first tank is between 1:1 to 1:20, or is between 1:2 to 1:20, or is between 1:3 to 1:20, or is between 1:4 to 1:20, or is between 1:5 to 1:20, or is between 1:6 to 1:20, or is between 1:7 to 1:20, or is between 1:8 to 1:20, or is between 1:10 to 1:20, or is between 1:1 to 1:15, or is between 1:2 to 1:15, or is between 1:3 to 1:15, or is between 1:4 to 1:15, or is between 1:5 to 1:15, or is between 1:6 to 1:15, or is between 1:7 to 1:15, or is between 1:8 to 1:15, or is between 1:10 to 1:15, or is between 1:1 to 1:10, or is between 1:2 to 1:10, or is between 1:3 to 1:10, or is between 1:4 to 1:10, or is between 1:5 to 1:10, or is between 1:6 to 1:10, or is between 1:7 to 1:10, or is between 1:8 to 1:10, or is between 1:9 to 1:10, or is between 1:3 to 1:7, or is between 1:3 to 1:8, or is between 1:3 to 1:9, or is between 1:4 to 1:7, or is between 1:4 to 1:8, or is between 1:4 to 1:9, or is between 1:5 to 1:7, or between 1:5 to 1:8, or between 1:5 to 1:9, or is between 1:3.5 to 1:5, or is between 1:4 to 1:5, or is between 1:1 to 1:3. , preferably 1:9, 1:7, 1:5 or more preferably 1:3 or 1:1.

Suitably, the protein in a protein-comprising precipitate after resuspension is at a concentration of about 5-100 g/L, preferably 10-50 g/L or more preferably 25-45 g/L. This includes 5, 10, 15, 20, 25, 30, 35, 40, 45, 50, 55, 60, 65, 70, 75, 80, 85, 90, 95 and 100 g/L and any ranges between these amounts. In other embodiments, the protein may be at a concentration of from about 5-20 g/L, e.g. about 8-12 g/L.

According to a preferred embodiment, the first suspension in the first tank or the second suspension (in the second or third tank) has a pH of between about 3.0 and 9.0, preferably between about 4.0 and 7.0, between about 4.0 to 6.0, between about 4.0 to 5.0, between about 4.3 to 4.9, between about 4.4 to 4.8, more preferably about 5.0. In general, the pH is measured either in the solution before adding the protein precipitate to the solution; or directly after mixing the protein precipitate with the solution. Typically, the pH of the solution is measured right after mixing the precursor components. Alternatively, the pH can also be determined by calculation based on the projected amounts and concentrations of the components in the mixture.

In certain embodiments, the conductivity of the first and second suspensions (and/or protein concentrates) may be adjusted. Typically, the conductivity of the protein suspensions or concentrates will be approximately 6 to 9 mS/cm, when the pH is in the range of between about 4.7 to 5.2, or adjusted to a similar conductivity prior to filtration.

In any aspect of the present invention, the first suspension may be continuously fed into the first filtration unit. In a preferred embodiment the first suspension is continuously fed into the first filtration unit until the first suspension has been diluted to at least the second dilution factor.

In the first aspect of the present invention, the second suspension may be continuously fed into the second filtration unit. In a preferred embodiment the second suspension is continuously fed into the second filtration unit until the second suspension has been diluted to at least the third dilution factor.

In the second aspect of the present invention, the second suspension may be continuously fed into the third filtration unit. In a preferred embodiment the second suspension is continuously fed into the third filtration unit until the second suspension has been diluted to at least the third dilution factor.

In another embodiment of the present invention, the process for obtaining a permeate/filtrate enriched for the protein of interest (for example, from the first and second suspensions) is via a continuous separation process. This process is adapted to separate impurities from the first suspension, to produce a filtrate enriched for the protein of interest and a retentate comprising one or more impurities. Further, the process is adapted to separate precipitant from the second suspension, to produce a further filtrate (e.g., a second filtrate in the first aspect of the invention, a third filtrate in the second aspect of the invention) which is enriched for the protein of interest. Preferably, the continuous separation process is a continuous filtration process where one or more filtration membranes or different types of filtration membranes can be used. The continuous filtration process such as a dynamic cross flow filtration can minimize the risk of the filtration members being blocked.

As the method of an aspect of the invention may involve adding additional liquid to the suspension in the first tank, the second dilution factor is greater than the first dilution factor.

According to an embodiment of an aspect of the present invention, the second and third dilution factors (volume of protein-comprising precipitate to volume of total recirculated liquid) are between 6 and 70, between 10 and 70, about 10, about 20, about 30, about 40, preferably about 20 to 50. In other embodiments the second and third dilution factors are about 60, or about 70 (1:70; parts protein-comprising precipitate:total). In particular embodiments the second and third dilution are at least 20, or at least 30, or at least 40, or at least 50, or at least 60, or at least 70. The inventor of the present invention found that such high dilution factors could enhance extraction efficiency, thus giving an improved yield.

In yet another embodiment, the predetermined value of protein concentration in the first suspension is less than 0.1 g/L, preferably between about 0.001 to 0.1 g/L; typically between about 0.05 to 0.1 g/L. Such value is provided such that the separation process can be terminated immediately once such threshold is reached in order to avoid inefficient extraction and filtration processes. For instance, when the total protein concentration in the first suspension is less than 0.1 g/L, the total amount of IgG is estimated to be less than about 40-50 mg/L, which makes it less economical to continue the continuous extraction and filtration of the product of interest.

In any aspect of the present invention, the dynamic filter element in the filtration unit adapted to produce a permeate enriched with the protein of interest (i.e., from the first or second suspensions) is a dynamic cross flow filter element. It will be understood that the first and second filter units comprise this filter element in the first aspect of the invention, and the first and third filter units comprise this filter element in the second aspect of the invention.

In a preferred embodiment the dynamic cross flow filter element is a rotational cross flow filter element. More preferably the rotational cross flow filter element comprises a filter disc. The filter discs are usually mounted on a shaft member. In an embodiment the rotational cross flow filter element comprises at least one filter disc and at least one shaft member.

According to a preferred embodiment of any aspect of the present invention, the filter disc membrane is a ceramic membrane. More preferably the ceramic membrane has a pore size in the range of greater than or equal to 5 nm to less than or equal to 2 μm. In particular embodiments, the ceramic membrane has a pore size of from about 0.2 μm to 2 μm. In particular embodiments, the ceramic filter membrane has an average pore size in the range of greater than or equal to 5 nm to less than or equal to 200 nm (0.2 μm). In particular embodiments, the ceramic filter membrane has an average pore size in the range of greater than or equal to 50 nm to less than or equal to 100 nm. Such filter discs are supplied by Kerafol and Flowserve.

The filtration unit in preferred embodiments comprises a pressure vessel. The suspension from the first tank can be continuously fed into the pressure vessel via an inlet port. An even distribution of the suspension in the vessel can be achieved using a distribution manifold. Hence in particular embodiments the pressure vessel comprises a distribution manifold.

In some embodiments the filtration unit adapted to produce a permeate enriched with the protein of interest from the first and/or second suspensions, comprises a rotational cross flow filter element. Preferably the filter element contains more than one filter disc evenly spaced along at least one hollow central collection shaft. The filter discs can be arranged either horizontally or vertically. When in the horizontal orientation they are spaced along a vertically orientated hollow collection shaft. The collection shaft and discs are rotatable. The suspension in the pressure vessel can then penetrate the outer membrane of the rotating filter discs so as to pass through into a hollow central portion of the disc which is in turn channeled into the central collection shaft. Typically the filtrate (i.e. the permeate enriched in the protein of interest) can then be removed from the shaft portion of the filtration unit via a flanged port, whilst the retentate (i.e., the retentate depleted for the protein of interest) remaining in the pressure housing can be fed out of the vessel via an outlet port. Generally the retentate is recirculated to the first tank or to the tank comprising the second suspension, in order to dilute the suspension. In this way the retentate from the first filtration unit can be utilised to dilute the suspension in the first tank to a second dilution factor. Further, in accordance with the first aspect of the invention, the retentate from the second filtration unit can be utilised to dilute the suspension in the tank comprising the second suspension. In accordance with the second aspect of the invention, the retentate from the third filtration unit can be utilised to dilute the suspension in the tank comprising the second suspension.

Dynamic cross flow filtration such as rotational filtration provides maximum filter efficiency. The cross flow effect (tangential flow cleaning of the filter surface) is generated by rotating the filter discs and not by pumping large volumes across a fixed membrane as used in conventional (static) cross flow filtration systems. The extreme cross flow velocities generated at the surfaces of the rotating filter discs ensure a highly efficient cleaning of the filter surface, whilst consuming very low amounts of energy compared to conventional cross flow techniques.

The temperature has an effect on the viscosity of a protein solution, the dissolution of the protein in suspension and also on the flux upon filtration with a membrane.

The starting suspension to be used in the method of the invention will preferably have a temperature within the range from 0° C. up to the temperature at which the protein concerned is denatured. The temperature suitably is within the range of from about 10° C. up to about 50° C. In particular embodiments the temperature is within the range of from about 18° C. up to about 35° C., preferably in the range of about 18° C. to about 22° C.

The temperature of the suspension tank comprising the agent for precipitating the one or more impurities in step e, will preferably have a temperature of between about 4° C. to about 40° C. Preferably the agent is a fatty acid, more preferably caprylic (octanoic) acid.

Accordingly, in any embodiment, the fatty acid, preferably caprylic (octanoic) acid is combined with the first permeate according to the first aspect of the invention, or with the second retentate of the second aspect of the invention, at a temperature of between about 4° C. to about 40° C. to generate the second suspension. In certain embodiments, the fatty acid, preferably caprylic (octanoic) acid is combined with the first permeate according to the first aspect of the invention, or with the second retentate of the second aspect of the invention (e.g., in the second suspension tank) at a temperature of between about 25° C. to about 38° C., about 27° C. to about 37° C., optionally about 27° C., about 32° C. or about 37° C. Optionally, both the first permeate according to the first aspect of the invention, or the second retentate of the second aspect of the invention and the fatty acid are at a temperature of between about 4° C. to about 40° C., preferably about 25° C. to about 38° C., about 27° C. to about 37° C., more preferably about 32° C. when they are combined.

The temperature in the filter units is controlled, preferably between 2° C. and 25° C., more preferably at about 2° C. to 15° C. Such temperature ensures an optimum extraction process and separation process while maintaining the bioreactivity of the protein of interest throughout the processes.

It will be appreciated that the temperature in the suspension tanks may be the same or different to the temperature in the filtration units. For example, while the permeate may be circulating in the filter units at one temperature, the temperature of the starting suspension may be higher than temperature at which filtration is performed. Similarly, the temperature of the permeate may be increased prior to and/or during the period of incubation with the fatty acid in the second suspension tank.

In one embodiment, the temperature in the first and second suspension tanks and in the filtration units is the same. In an alternative embodiment, the temperature in the first suspension tank and in the filtration units is lower than the temperature in the second suspension tank.

Filtration is performed with a transmembrane filtration pressure that is the same as or below the level at which the membrane can withstand, depending on the material of the membrane to be used herein, for example with pressures of about 0.2 to about 3 bar. The transmembrane pressure is typically from 0.1 to 2.5 bar, preferably from 0.2 to 2.4 bar, more preferably from 0.4 to 2.0 bar, from 0.5 to 1.8 bar, from 0.6 to 1.6 bar, from 0.6 to 1.5 bar, from 0.7 to 1.5 bar, most preferably from 0.8 to 1.5 bar. According to another embodiment, a pressure of up to 2 bar, preferably between 0.1 to 2.0 bar, or about 1.5 bar, 1.0 bar or 0.5 bar is provided to filter units.

According to another embodiment, the continuous extraction process in the filter units adapted to separate impurities/precipitant from the first and second suspensions, is further assisted by regulating the flow rate and/or the residence time of the suspension or the solution into the filter units and/or the flow rate of the retentate/raffinate comprising impurities/precipitant and/or the flow rate of the first permeate/filtrate enriched for the protein of interest. For instance, in one embodiment, the linear velocity of the suspension or the solution into the pressure vessel (filtration process unit) can be about 0.27 to 1.66 m/s. In another example, the linear velocity of the retentate comprising impurities/precipitant can be 0.25 to 1.33 m/s. In another example, the linear velocity of the permeate/filtrate enriched for the protein of interest can be 0.03 to 0.33 m/s. Linear velocity multiplied by the cross-sectional area gives the volumetric flow rate. In addition, a turbulence can be created in the first process unit as a result of the speed of the rotating filter discs, wherein the speed (sometimes referred to as tangential speed) can be between about 1 to 7 m/s. According to an embodiment of the present invention, the speed of the rotating disc filters is between 1 to 10 m/s. In a preferred embodiment of the present invention, the speed of the rotating disc filters is between 5 to 7 m/s. More preferably the speed of the rotating disc filters is 7 m/s at 60 Hertz (800 rpm). The rotating speed of the rotational cross-filter element is between about 600 rpm (50 Hz) and about 1600 rpm (100 Hz), preferably between about 800 rpm (60 Hz) and about 1200 rpm (80 Hz), preferably about 800 rpm (60 Hz), about 1000 rpm (70 Hz) or about 1200 rpm (80 Hz). As used herein, the rotating speed in Hz is intended to refer to the speed of the motor. This can be correlated with the speed in rpm using an appropriate calibration curve.

This method allows a continuous extraction and a separation process to be realised for maximising the recovery of the protein of interest from the starting precipitate/material (i.e., the first suspension) or from the second suspension. Thanks to the extraction process, almost all the protein of interest is extracted from the protein-comprising precipitate and is recovered in subsequent stages. This method also allows the liquid or diluent e.g. buffer or water to be re-circulated in a closed system and hence the quantity of the liquid is maintained throughout the process while footprints (i.e. large tank volume) can be reduced.

In still further embodiments, the present invention includes a step of backflushing in conjunction with dynamic crossflow filtration. As used herein, the term "backflushing" will be understood to refer to a process where the flow of liquid into the filtration system is reversed, in order to flush contaminants that may have built up in the system. Preferably, the backflushing is performed with the same buffer comprised in the first or second suspensions. It will be understood that the frequency, duration and flow rate of the backflushing can be adjusted in order to maximize filtration efficiency and the period of filtration before backflushing is required, as further described herein.

It is estimated that the method and the system disclosed herein recovers at least 75%, at least 80%, at least 85%, at least 90%, at least 95%, or typically at least 98% of the protein of interest in the protein-comprising precipitate. Hence, in particular embodiments of the first aspect of the present invention, the method provides a recovery of at least 95%, or at least 96%, or at least 97%, or at least 98% or at least 99% of the protein of interest from the precipitate. In a preferred embodiment the recovery is at least 97% of the protein of interest from the precipitate.

The first permeate/filtrate enriched for the protein of interest can be subjected to a concentration step prior to the step of precipitating the impurities in the first permeate. The concentration process may be an ultrafiltration performed in a second filtration unit, for example as outlined in steps d1 to d3 of the second aspect of the invention. Alternatively, the concentration process may be using any standard concentration technique, including dialysis, filtration (including ultrafiltration), chromatography or precipitation.

According to an embodiment of the first aspect of the present invention the method additionally comprises subjecting the second permeate (in a second tank), enriched for the protein of interest, to a continuous concentration process in a third filtration unit, thereby producing a third retentate enriched with the protein of interest and a third permeate depleted of the protein of interest.

According to an embodiment of the second aspect of the present invention, the method additionally comprises subjecting the third permeate enriched in the protein of interest to a continuous concentration process in a fourth filtration unit, thereby producing a fourth retentate enriched for the protein of interest and a fourth permeate depleted for the protein of interest.

According to an embodiment of the first and second aspects of the present invention the filtration unit for performing the continuous concentration process comprises a dynamic cross flow filter element including a dynamic ultrafiltration filter device. Alternatively, the process comprises a static ultrafiltration device.

In preferred embodiments of the invention the dynamic cross flow filter element or the ultrafiltration filter device for performing the concentration process comprises a membrane with a molecular weight cutoff less than the molecular weight of the protein of interest. In these embodiments the membrane cutoff is selected to retain the protein of interest during the concentration process. As a general guide a nominal membrane cutoff at least 3-fold lower than the molecular weight of the protein of interest can be selected to ensure the protein is retained in the retentate.

In one alternative embodiment the dynamic cross flow filter element or the static ultrafiltration filter element for performing the concentration process comprises a membrane with a molecular weight cutoff greater than the molecular weight of the protein of interest. In such embodiments the nominal membrane cutoff is selected to ensure the protein of interest passes across the membrane and is collected in the second or fourth permeates rather than the second or fourth retentates (in the case of the second aspect of the invention) or in the third permeate rather than third retentate (in the case of the first aspect of the invention).

In embodiments where the cross flow filter element is dynamic, preferably the element is a rotational cross flow filter element, adapted for performing a continuous concentration process.

According to a further preferred embodiment, the filtration element for performing the continuous concentration process comprises a filtration membrane having an average pore size of between 5 nm to 5000 nm, preferably between 5 nm to 2000 nm, between 5 nm to 1000 nm, between 5 nm to 500 nm, between 5 nm to 200 nm, between 7 nm to 1000 nm, more preferably between 7 nm to 500 nm, even more preferably between 7 nm to 100 nm, most preferably between 7 nm to 80 nm. Of course, the average pore size can be in other combinations of the range given above. Filter manufacturers often assign terms like nominal or mean pore size ratings to commercial filters, which usually indicate meeting certain retention criteria for particles or microorganisms rather than the geometrical size of the actual pores.

In a particular embodiment the rotational cross flow filter element for performing the continuous concentration process comprises a filter disc (such as a ceramic disc). In some embodiments the filter disc comprises a membrane with an average pore size of a microfilter. In other embodiments the filter disc comprises a membrane with an average pore size of an ultrafilter. In further embodiments, the filter disc comprises a membrane with an average pore size of a diafilter. In an embodiment the average pore size of the filter disc membrane is in a range from greater than or equal to 5 nm to less than or equal to 2 μm. In particular embodiments the average pore size of the filter disc membrane is in a range from greater than or equal to 50 nm to less than or equal to 0.5 μm. In some embodiments the filter disc membrane has an average pore size in the range of greater than or equal to 50 nm to less than or equal to 100 nm, or in the range of greater than or equal to 60 nm to less than or equal to 90 nm, or in the range of greater than or equal to 60 nm to less than or equal to 80 nm. In some embodiments, the filter disc membrane has an average pore size of 60 nm or 80 nm.

In particularly preferred embodiments, the rotational cross flow filter element for performing the continuous concentration process comprises a plurality of ceramic discs with a pore size suitable for ultrafiltration and/or diafiltration. For example, the element preferably comprises at least one ceramic membrane having a pore size of 3 nm. Alternatively, the element preferably comprises at least one ceramic membrane having a pore size of 5 nm. Alternatively, the element preferably comprises at least one ceramic membrane having a pore size of 7 nm. Alternatively, the element preferably comprises at least one ceramic membrane having a pore size of 30 nm. The element may comprise a plurality of ceramic discs with varying pore sizes, including wherein the pore sizes are 3 nm and 5 nm. The element may comprise a plurality of ceramic discs with varying pore sizes, including wherein the pore sizes are 5 nm and 7 nm. The element may comprise a plurality of ceramic discs with varying pore sizes, including wherein the pore sizes are 3 nm and 30 nm. The element may comprise a plurality of ceramic discs with varying pore sizes, including wherein the pore sizes are 3 nm, 5 nm, 7 nm and 30 nm.

According to yet a further preferred embodiment, a filtration element for performing the continuous concentration process comprises an ultrafiltration device comprising a membrane in the form of a polymer membrane, such as polyethersulfone or regenerated cellulose. Such membranes preferably have an average molecular weight cutoff value of less than 50 kDa, preferably less than 30 kDa, more preferably less than 10 kDa or most preferably less than 5 kDa.

According to an embodiment of the first aspect of the present invention, the method further comprises diluting the suspension in the tank comprising the second suspension by continuously streaming the second permeate and/or second retentate depleted in the protein of interest to the tank comprising the second suspension, thereby contributing to the suspension being diluted to the third dilution factor.

Similarly, according to an embodiment of the second aspect of the present invention the method further comprises diluting the suspension in the tank comprising the second suspension by continuously streaming the third permeate and/or third retentate depleted in the protein of interest to the tank comprising the second suspension, thereby contributing to the suspension being diluted to the third dilution factor.

According to an embodiment of an aspect of the present invention the method further comprises diluting the suspension in the first tank by continuously streaming the retentate from the first filtration unit and the second permeate from the second filtration unit into the first tank, thereby diluting the suspension to the second dilution factor.

According to yet a further preferred embodiment of the first aspect of the invention, a second tank is provided to receive the first permeate, wherein the flow velocity of the first permeate is controlled such that a substantially constant product volume is maintained in the second tank. In particular embodiments fresh buffer is added to the first tank in addition to the first permeate.

According to yet a further preferred embodiment of the second aspect of the invention, a second tank is provided to receive the first permeate and/or the second retentate, wherein the flow velocity of the first permeate and second retentate is controlled such that a substantially constant product volume is maintained in the second tank. In particular embodiments fresh buffer is added to the first tank in addition to the first permeate and/or second retentate.

According to yet a still preferred embodiment of the second aspect of the invention, a further (fourth) tank is provided to receive the third permeate and/or the fourth retentate, wherein the flow velocity of the third permeate and fourth retentate is controlled such that a substantially constant product volume is maintained in the tank comprising the second suspension.

According to an embodiment of an aspect of the present invention, the first permeate/extract/filtrate is collected in a holding tank (second tank), and once the suspension of the first tank is completely filtered/extracted, the first permeate/extract from the holding tank is subjected to the continuous concentration process. Such a method step is especially suitable for a smaller industrial scaled process where dead volumes in the production equipment and tubing can significantly impact the yield of the protein of interest. An example is hyperimmune immunoglobulin products.

According to a preferred embodiment of the second aspect of the invention, there is provided an industrial scaled method for extracting a protein of interest in high yield from a precipitate, comprising:
- a) mixing the precipitate with a liquid in a first tank to form a suspension having a first dilution factor;
- b) feeding the first suspension into a first filtration unit comprising a rotational cross flow filter element comprising a filter disc having a ceramic membrane with an average pore size between 5 nm and 5000 nm, the filter element adapted to produce a first retentate depleted of the protein of interest, and a first permeate enriched with the protein of interest;
- c) diluting the first suspension in the first tank by adding liquid to a second dilution factor in part by streaming the first retentate into the first tank;
- d) recovering the first permeate enriched with the protein of interest in a second tank; and
- e) subjecting the first permeate in the second tank to a continuous concentration process in a second filtration unit comprising a cross flow filter element, thereby producing a second retentate enriched with the protein of interest and a second permeate depleted of the protein of interest;
- f) optionally diluting the first suspension in the first tank by continuously streaming the second permeate to the first tank, thereby diluting the suspension to the second dilution factor; and g) either returning the second retentate enriched with the protein of interest to the second tank and/or collecting the second retentate enriched with the protein of interest.

h) precipitating one or more impurities in the second retentate enriched with the protein of interest to produce a second suspension; and i) removing the precipitated impurities from the second suspension to produce a solution containing the protein of interest.

The precipitated impurities can be removed from the second suspension according to a method as herein described, including by feeding the second suspension into a third filtration unit comprising a dynamic filter element adapted to produce a third retentate containing the one or more precipitated impurities and a third permeate enriched with the protein of interest; optionally streaming the third retentate into the tank comprising the second suspension; recovering the third filtrate enriched with the protein of interest in a further tank.

Preferably, removing the precipitated impurities from the second suspension to produce a solution containing the protein of interest further comprises: subjecting the third permeate in the further tank to a continuous concentration process in a fourth filtration unit comprising a cross flow filter element, thereby producing a fourth retentate enriched with the protein of interest and a fourth permeate depleted of the protein of interest; optionally diluting the suspension in the tank comprising the second suspension by streaming the fourth permeate to the tank comprising the second suspension, thereby diluting the suspension to a third dilution factor; and either returning the fourth retentate enriched with the protein of interest to the further tank and/or collecting the fourth retentate enriched with the protein of interest.

According to a preferred embodiment of this aspect of the invention, the first retentate and the second permeate are continuously streamed into the first tank to dilute the suspension to the second dilution factor. Further, the third retentate and fourth permeate may be continuously streamed into the tank comprising the second suspension, in order to dilute the second suspension to a third dilution factor.

According to an embodiment of the invention the filtration unit adapted to produce a permeate enriched for the protein of interest comprises more than one hollow shaft adapted to collect the permeate, each shaft connected to at least one filter disc comprising a ceramic membrane.

According to an embodiment of the invention the filtration unit for performing the concentration process comprises a dynamic cross flow filter element. In other embodiments the filtration unit comprises a static cross flow filter element. In a preferred embodiment the static cross flow filter element is an ultrafiltration device comprising a membrane that retains the protein of interest in the retentate.

According to an embodiment of the present invention, either the steps b) to c) or the steps b) to f) are repeated until either a second dilution factor or a predetermined value of protein concentration of the suspension or the solution in the first tank has been achieved. Such predetermined second dilution factor (sometimes referred to as a final dilution factor), which can also be determined using a predetermined value of protein concentration the tank comprising the first suspension ensures that an optimal yield can be harvested before it becomes too uneconomical to continue the extraction process. Protein concentration can be monitored in the tank comprising the first suspension by various methods known in the art including UV absorbance, such as at 280 nm.

Optionally a filter aid may be employed at appropriate stages of the process. A filter aid may be used, for example, in one or more steps involved in preparation of the precipitate. Accordingly, in one embodiment, the precipitate comprises a filter aid. In one embodiment, the precipitate does not comprise a filter aid. In this embodiment, a filter aid may not have been used in the process at all (including in any preceding steps), or, if present, is removed prior to feeding the suspension comprising the precipitate into the first filtration unit i.e. before step b). Preferably, the filter aid is removed prior to step b).

The product of the methods described above may then be subjected to further processing including one or more of chromatography steps, virus inactivation steps, concentration and formulation such that the end product is suitable for administration to a subject, preferably a human subject.

According to an embodiment of the aspects of the invention the filtration unit adapted to produce a permeate enriched for the protein of interest (i.e., the first and second filter units in the first aspect of the invention, or the first and third filter units in the second aspect of the invention) further comprises a scraper device adapted to control the bed height of filter aid and/or precipitate material on an outer surface of a filter disc membrane. This device can also assist in controlling filtration flux rates and/or prevent filter blockage. In some embodiments the scraping device is height adjustable with respect to the distance to the surface of the filter disc membrane. In particular embodiments the scraping device is positioned at least 20 cm, or at least 15 cm, or at least 10 cm, or at least 9 cm, or at least 8 cm, or at least 7 cm, or at least 6 cm, or at least 5 cm, or at least 4 cm, or at least 3 cm, or at least 2.5 cm, or at least 2 cm, or at least 1.5 cm, or at least 1 cm, or at least 0.5 cm, or at least 0.25 cm from a filter disc membrane.

According to a further embodiment, the filtration process units are equipped with rotating filter discs (dynamic filter element) and optionally baffle for turbulence mixing of the content of the first filter unit, preferably the tangential speed of the disks is between about 1 to 7 m/sec.

Turbulences can be produced by the baffles such that extraction of the protein of interest can be increased, thereby high protein recovery yield is achieved.

In preferred embodiments of the invention, the rotational cross flow filter elements comprise one or more filter discs comprising a ceramic membrane.

Ceramic filters can be for example composed of $Al_2O_3$, or $ZrO_3$, $TiO_2$ or $MgAl_2O_4$. Ceramic disc filters are typically designed so that filtrate is transported across the ceramic membrane from the outside into a hollow inner channel from which the filtrate can be collected.

Ceramic disc filters are available in various sizes including with outer diameters of 374 mm (surface area 0.2 m$^2$), 312 mm (surface area 0.14 m$^2$) and 152 mm (surface area 360 cm$^2$). Typically, the ceramic disc filters have a thickness ranging from about 4.5 to 6 mm.

In embodiments of the invention, the first and third units have a filter capacity that is at least 25 kg or at least 50 kg or at least 75 kg or at least 100 kg or at least 200 kg or at least 300 kg or at least 350 kg or at least 400 kg or at least 450 kg or at least 500 kg or at least 550 kg or at least 600 kg or at least 650 kg or at least 700 kg or at least 750 kg or at least 1000 kg of the starting precipitate per m$^2$ of filter surface area.

In a further aspect, the present invention provides a method for precipitating one or more impurities from a solution containing a protein of interest, the method comprising a) providing a solution containing a protein of interest and one or more impurities, wherein the solution has a conductivity of 6 to 9 mS/cm, pH 4.7 to 5.2 and a total protein concentration of 15 to 17 g/L; and b) precipitating one or more impurities by adding a fatty acid to the solution, wherein the fatty acid is added at an amount of about 0.1 g to about 0.4 g fatty acid/g of total protein.

In a further aspect, the present invention provides a method for removing one or more impurities from a solution containing a protein of interest, the method comprising a) providing a solution containing a protein of interest and one or more impurities, wherein the solution has a conductivity of 6 to 9 mS/cm, pH 4.7 to 5.2 and a total protein concentration of 15 to 17 g/L;

b) precipitating one or more impurities by adding a fatty acid to the solution, wherein the fatty acid is added at an amount of about 0.1 g to about 0.4 g fatty acid/g of total protein;

c) removing the one or more precipitated impurities.

In still a further aspect, the present invention provides a method for removing one or more impurities from a solution containing a protein of interest, the method comprising a) providing a solution containing a protein of interest and one or more impurities, wherein the solution has a conductivity of 6 to 9 mS/cm, pH 4.7 to 5.2 and a total protein concentration of 15 to 17 g/L;

b) optionally subjecting the solution to filtration in a filtration unit comprising a rotational cross flow filter element to obtain a permeate enriched with the protein of interest;

c) precipitating one or more impurities by adding a fatty acid to the solution, preferably to the permeate enriched with the protein of interest, wherein the fatty acid is added at an amount of about 0.1 g to about 0.4 g fatty acid/g of total protein;

d) removing the one or more precipitated impurities.

Advantageously, the above methods enable recovery of the protein of interest such that less than about 1%, about 2%, about 3%, about 4%, about 5%, about 6%, about 7%, about 8%, about 9%, less than about 10% or less than about 20% of the protein of interest is lost during the process of removing the one or more impurities.

Preferably, the fatty acid comprises a general structural formula of $CH_3(CH_2)_nCOOH$. More preferably, the fatty acid is a C 7 to C 10 carboxylic acid. More preferably, the fatty acid comprises enanthic (heptanoic) acid, caprylic (octanoic) acid, octenoic acid, pelargonic (nonanoic) acid, nonenoic acid, or capric (decanoic) acid. Most preferably, the fatty acid is caprylic (octanoic) acid. Also contemplated as the reagent is a salt or ester of any fatty acid described herein.

In any embodiment of an aspect of the invention, the amount of fatty acid, preferably caprylic (octanoic) acid, is about 0.1 g/g total protein, about 0.5 g/g total protein, about 0.75 g/g total protein, about 1 g/g total protein, about 1.5 g/g total protein, about 2.0 g/g total protein, about 2.5 g/g total protein, about 3.0 g/g total protein, about 3.5 g/g total protein, or about 4.0 g/g total protein. Preferably, the amount of fatty acid, preferably caprylic (octanoic) acid, is about 0.275 g/g total protein, about 0.280 g/g total protein, about 0.285 g/g total protein, about 0.290 g/g total protein, about 0.300 g/g total protein, about 0.325 g/g total protein, or about 0.35 g/g total protein.

In any embodiment of an aspect of the invention, the amount of fatty acid, preferably caprylic (octanoic) acid, is 0.1 g/g total protein, 0.5 g/g total protein, 0.75 g/g total protein, 1.0 g/g total protein, 1.5 g/g total protein, 2.0 g/g total protein, 2.5 g/g total protein, 3.0 g/g total protein, 3.5 g/g total protein, or 4.0 g/g total protein. Preferably, the amount of fatty acid, preferably caprylic (octanoic) acid, is 0.275 g/g total protein, 0.280 g/g total protein, 0.285 g/g total protein, 0.290 g/g total protein, 0.300 g/g total protein, 0.325 g/g total protein, or about 0.35 g/g total protein.

In any embodiment of an aspect of the invention, the solution may be a fraction from a plasma fractionation process. Preferably, the solution is obtained or obtainable from steps a) to d) (optionally including steps d1 to d3) as described in a method of the invention.

In any embodiment of an aspect of the invention, the solution does not contain filter aid.

In any embodiment of an aspect of the invention, the protein of interest is an immunoglobulin, preferably human immunoglobulin G (IgG) such as immunoglobulin G from human plasma or a recombinantly produced immunoglobulin G.

In any embodiment of an aspect of the invention, the solution contains IgG.

In any embodiment of an aspect of the invention, the solution contains one or more of the following impurities: IgA, IgM, albumin, $\alpha$(alpha)-2 macroglobulin, $\alpha$(alpha)-1 anti-trypsin, a lipid, and a lipoprotein.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

BRIEF DESCRIPTION OF THE DRAWINGS

The following drawings are not necessarily drawn to scale; emphasis instead is generally being placed upon illustrating the principles of various embodiments. In the following description, various embodiments of the invention are described with reference to the following drawing:

FIG. 1 illustrates a schematic flow chart overview of the system 100 and the method according to one preferred embodiment of the present invention. Protein-comprising precipitate e.g. in form of a suspension, or in form of a paste or precipitate is suspended with liquid e.g. buffer. The compositions and concentration of the buffer are in accordance with the above described method in order to generate a starting composition such as a suspension having a first dilution factor e.g. between 3 to 10 (1:3 to 1:10). The suspension is housed in a first tank 1. The suspension can be fed to a first filtration unit 5, through the pump 2, several type of pumps can be used (e.g. piston-; rotary-; centrifugal- and membrane pump) and flow-regulated valve 3 of a pipe 12. The first filtration unit 5 is equipped with a rotating hollow shaft to which the filter discs are mounted (the filtrate flows from the outside to the inside of hollow shaft). The first filtration unit 5 is further set up with height adjustable scrapers to keep the filter cake thickness constant and thus achieve constant filtrate flow. The desired filtration pressure is controlled and regulated by overflow valve (unfiltered suspension outlet). The filter discs used can be a ceramic membrane, depth filter layers and sintered porous metal filter discs. Once the vessel of the first filtration unit 5 is filled with the suspension, a continuous pressure extraction and separation can be started. The first filtration unit 5, which can comprise a pressure unit/vessel, is provided with suitable internal settings and conditions to simultaneously increase the extraction efficiency and filtration process. The extraction efficiency is increased through turbulence mixing in the unit 5 without having to involve a mixer. Nevertheless, it can be foreseen that an additional mixer may be provided to assist the extraction process by creating turbulences. Moreover, higher final dilution factor e.g. 40 or 70 disclosed in the present invention also increases the extraction efficiency, leading to high protein (e.g. IgG) yield. Of course, any other higher final dilution factor (higher than 70) can also be envisaged.

Figure 1:
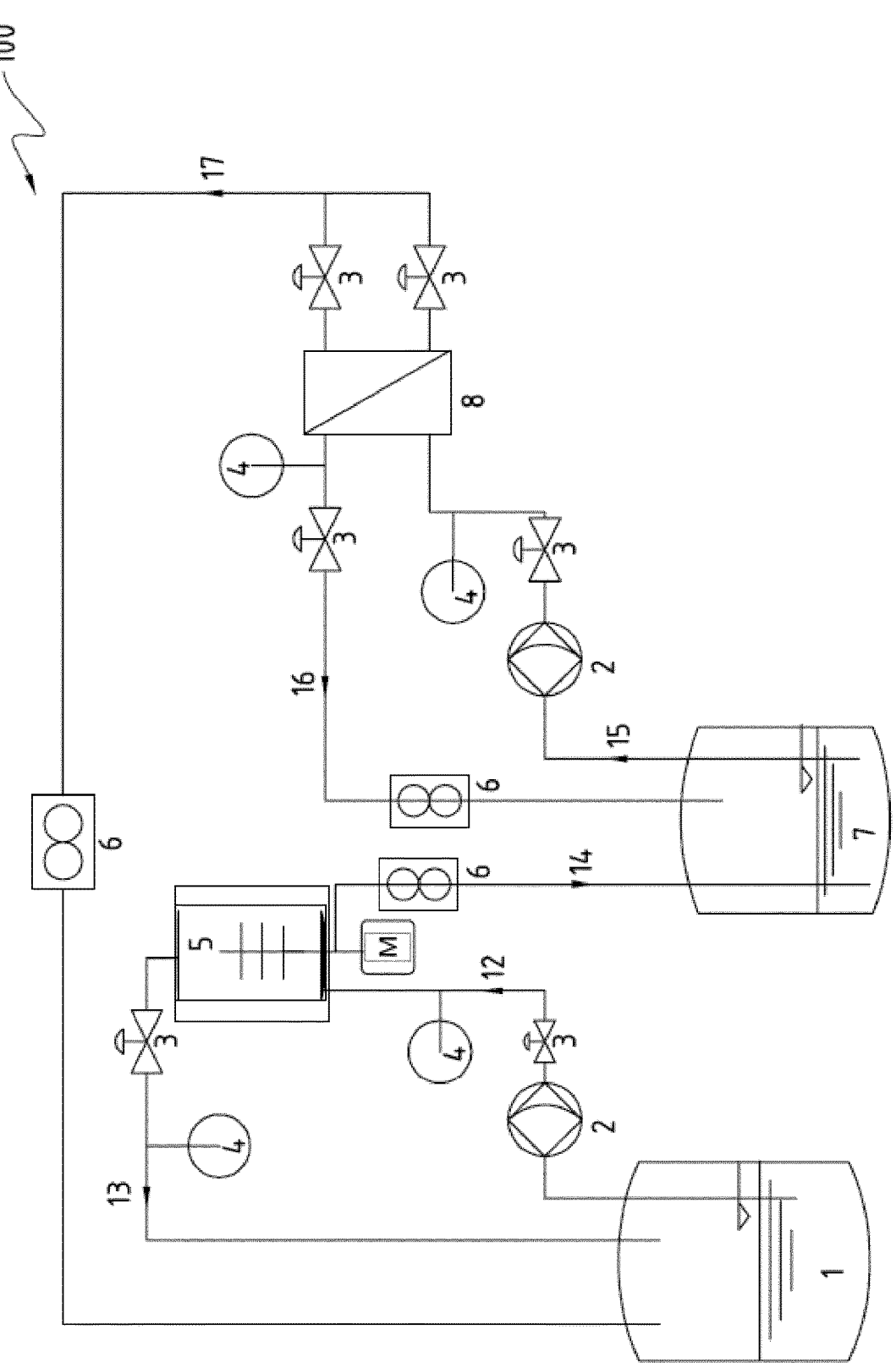
FIG. 1 is a schematic flow chart overview of the system of the present invention, and is described in more detail below.

The filtrate flows through a flowmeter 6 installed on pipe (or channel) 14 and is collected in the second tank 7. The unfiltered suspension flows back through the regulated outlet 3 installed on pipe 13 in tank 1. When a defined volume in the second tank 7 is reached, the UF 8 concentration process can be started in the second filtration unit. The filtrate in the second tank 7 flows through pipe 15 into the ultrafiltration (UF) system 8. The transmembrane pressure is set such that the permeate flow rate 17 is identical or almost identical to that with the first filtrate flow rate in pipe 14. The permeate of the UF system 8 flows through pipe (or line or channel) 17 back to the first tank 1, whereas the retentate of the UF system (=concentrated protein) flows through pipe 16 back to the second tank 7.

In accordance with the invention, the first process unit 5 is provided with one or more rotating filter discs comprising one or more of the first filter element for turbulence mixing of the content of the first process unit 5 for producing the first retentate and the first permeate. The first retentate can be fed back to the first tank 1 through a channel 13 via a control valve 3 whereas the first permeate can be fed to a second tank 7 via another channel 14. The first filter element can be a filtration membrane which is based on a ceramic material, having a pore diameter of between about 5 nm to 5000 nm, preferably between 20 nm to 100 nm or more preferably between 30 nm to 80 nm. It can also be foreseen that inorganic membranes or any other suitable membranes could also provide a similar effect as the ceramic based membrane. The first filtration unit 5 may be supplied with a pressure control device 4 such as a manometer in order to regulate the pressure within. Similarly, a flowmeter 6 can be installed in the system of the present invention for measuring the flow rate of the suspension or solution.

Feedstream from the second tank 7 can then be fed to a second filtration unit 8 through a channel 15 for a second separation process to be carried out. The second separation process can be a continuous concentration process (e.g. UF). The second filtration unit 8 is provided with one or more second cross flow filter element/s, wherein the second cross flow filter element can comprise an ultrafiltration membrane having an average molecular weight cutoff value of less than 50 kDa. However, the membrane can also be less than 10 kDa or more preferably less than 5 kDa. The ultrafiltration membrane therefore produces a second retentate which is channeled back to the second tank 7 through a channel 16 whereas the second permeate is fed to the first tank 1 via a channel 17. To this end, it is noted that the pressure of the second filtration unit 10 can be regulated during concentration step (ultrafiltration) such that the flow velocity of channels 14 and 17 are substantially equal.

Figure 2:
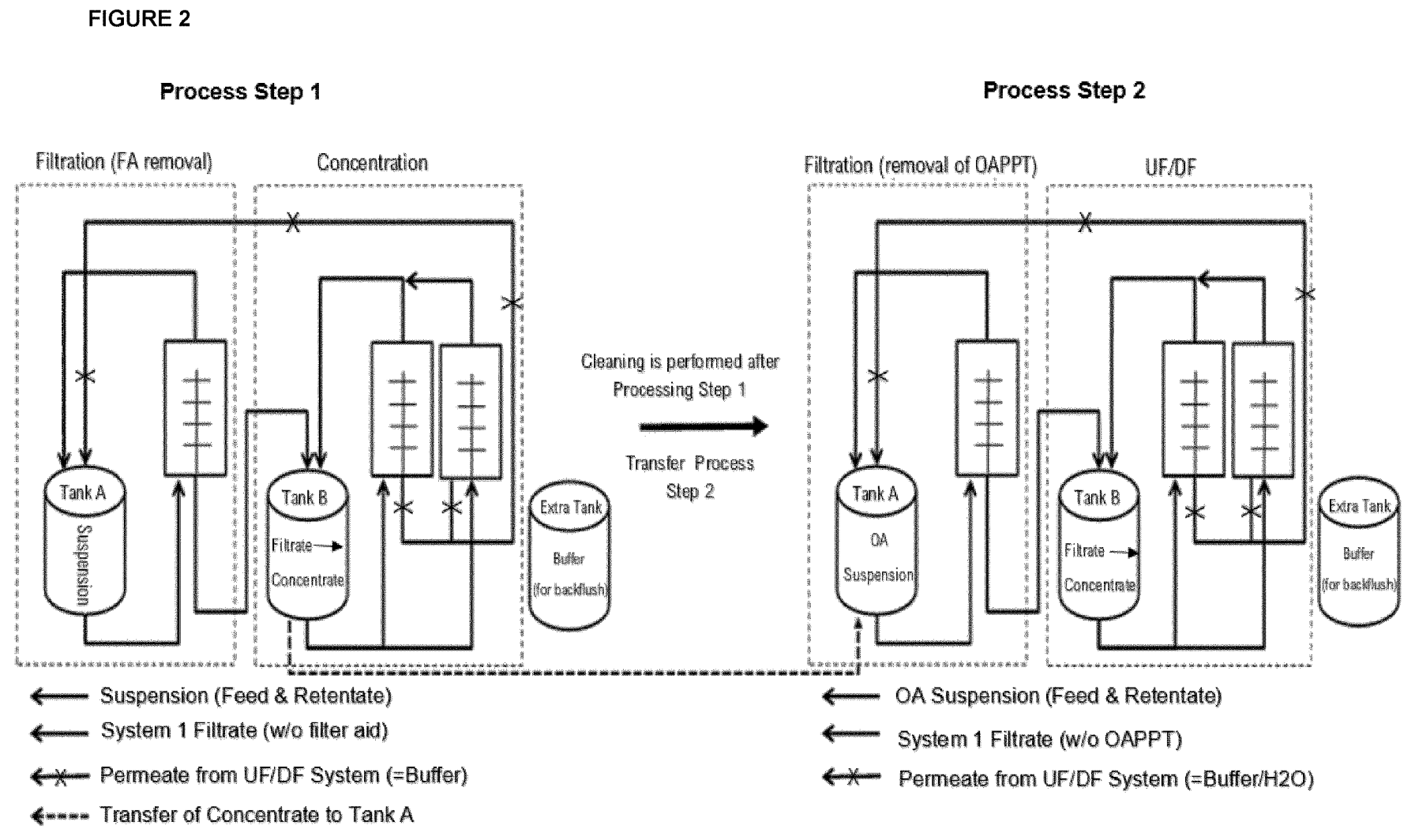

FIG. 2 is a schematic overview of a further system of the present invention, and is described in more detail below.

DETAILED DESCRIPTION OF THE EMBODIMENTS

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

For purposes of interpreting this specification, terms used in the singular will also include the plural and vice versa.

The present invention relates to a system and a method for maximising protein recovery and yield by using a novel first process unit or further with a second process unit, and a precipitating step to remove one or more impurities. The combination of an extraction and separation method, in conjunction with a precipitating step is used in the present invention to process a solid protein-comprising precipitate i.e. an intermediate material (e.g. paste derived from a starting material) wherein the starting precipitate may be suspended in a liquid or diluent e.g. water or buffer, to form a suspension.

One advantage of the methods of the present invention is that the total recovery of a protein of interest is maximized such that there is minimal loss of this protein during the steps required to remove impurities and other proteins which are not of interest. These advantages arise, in part, from the application of a continuous extraction filtration method, in combination with subsequent precipitation steps. The continuous extraction method facilitates downstream processing using conditions which minimize loss of the protein of interest, for example, by reducing the total amount of reagent required to precipitate impurities or proteins that are not of interest.

Typical protein containing precipitates are formed during the purification of proteins after exposure to precipitants such as ethanol. The solid is often called the precipitate or paste. The precipitate can be mixed with liquid to form a suspension in which solid particles are distributed throughout the liquid. Under particular extraction conditions the protein contained in these particles can be progressively dissolved into the liquid phase.

The dissolution ratio in industrial scaled manufacturing processes poses a problem because of the large volume of water or buffer required. For plasma fractionation processes used to manufacture proteins like albumin and immunoglobulins this step can involve many thousands of litres. Even when tanks are available to hold such large volumes to enable large dissolution ratios, the desired effect of higher yield can fail to materialize because of an equilibrium (Le Chatelier's principle) between protein dissolved in the solution and that remaining in the precipitate or paste. Such protein trapped in the precipitate may not be recoverable for further processing to final product. This phenomenon is related in part to the solubility equilibrium. As a known solubility equilibrium exists when a compound in the solid phase is in chemical equilibrium with the compound dissolved in the solution. The equilibrium is an example of a dynamic equilibrium in that some individual molecules migrate between the solid and liquid phases such that the rates of dissolution and precipitation are equal to one another.

This invention aims to solve the problem of protein recovery from precipitates by (a) continuously shifting the solubility equilibrium, and (b) precipitating one or more impurities. Continuously shifting the solubility equilibrium is achieved by: 1) increasing the extraction efficiency (using dynamic filtration system which can incorporate hollow rotating disk filter elements) with built-in components to allow intimate phase contact in a repetitive way; 2) continuously removing dissolved protein from the protein containing precipitate (by applying Le Chatelier's principle—when any system at equilibrium is subjected to change in concentration (e.g. volume), temperature, or pressure, then the system re-adjusts to counteract (partially) the effect of the applied change and a new equilibrium is established. This means by continuously increasing the volume at the resuspension site and continuously removing the dissolved protein through the dynamic filter, Le Chatelier's principle can be utilized to ensure maximum protein transfer from the precipitate into the liquid phase. In some instances, increased volume can be realized by recycling the permeate during a continuous concentration step of the protein, thereby reducing consumption of buffer. Further, precipitating one or more impurities is achieved by altering the solvation potential of the solvent, more specifically, by lowering the solubility of the one or more impurities by addition of a reagent and/or modulating the conditions (e.g. like pH or conductivity). The result is a greater recovery of a protein of interest with the same, substantially the same or reduced, nature and/or amount of impurities. In other words, the step of precipitating one or more impurities in the context of the invention results in a greater recovery of a protein of interest with the same, substantially the same or reduced, nature and/or amount of impurities, than if that precipitating step was not performed.

In addition, the present invention also relates to the identification that significantly reduced amounts of reagent that lowers the solubility of one or more impurities can be used to precipitate the one or more impurities from a solution containing a protein of interest. In particular, the lower amounts of reagent can be used when the solution containing a protein of interest has certain characteristics. The advantage is that process costs can be reduced by using lower amounts of a reagent as well as a greater recovery of a protein of interest as the amount of protein of interest that is co-precipitated with the one or more impurities is reduced.

Definitions

The term "protein-comprising precipitate" is intended to refer to any material containing the protein of interest. In the context of immunoglobulin as the protein of interest, this term may refer to plasma, serum, precipitates produced from plasma or serum, fermentation broths, inclusion bodies, cell culture supernatants, or precipitates produced from such materials. Typically, in the context of the present invention, it refers to precipitates from plasma, such as Cohn or Oncley ethanol precipitates, or Kistler-Nitschmann precipitates.

The term "starting composition" refers to a suspension or solution, produced from the protein-comprising precipitate, typically by dilution with water or buffer according to a (first) dilution factor. In some instances, if no dilution of the protein-comprising precipitate is required, the protein-comprising precipitate may be the starting suspension.

By "high yield" it is meant that the yield of the protein of interest such as immunoglobulin G (as well as other proteins and immunoglobulins) is at least 95% of the amount of the protein of interest in the protein-comprising precipitate, preferably at least 96%, more preferably at least 98%, most preferably more than 98%.

The concentration of immunoglobulin in a sample (e.g., in the precipitate or in a pharmaceutical-grade purified preparation thereof) can be measured by any means known to persons skilled in the art. It will be understood that the method used to measure immunoglobulin may depend on the nature of the sample. For example, it will be understood that, where the sample is an immunoglobulin-containing precipitate, it may be necessary to dissolve the precipitate (or a sample thereof) in a suitable buffer prior to the measurement. Examples of suitable assays for measuring a protein of interest include high pressure liquid chromatography (HPLC; e.g., size exclusion HPLC), enzyme-linked immunosorbent assay (ELISA) and quantitative immunonephelometry.

By "about" or "approximately" in relation to a given numerical value for percentage, pH, amount or a period of time or other references, it is meant to include numerical values within 10% of the specified value.

Large or Industrial Scale Processes or Systems

Large or industrial scale with regard to the present invention represents production procedures based on at least 200 L, preferably at least 500 L, even more preferably at least 2000 L of a starting material such as human plasma. For example typical commercial plasma donor pool sizes used in industrial scaled protein manufacture range from 2500 L to 6000 L of plasma per batch. In particular embodiments of the invention the precipitate is obtained from 2500 L to 6000 L of plasma. Some commercial manufacturing processes are capable of using even larger plasma donor pool sizes including up to 7500 L, up to 10000 L, and/or up to 15000 L of plasma.

The method and system of the invention can also be used not only for large industrial scale applications but as a stand-alone system and/or method for smaller production scale applications (where the starting material may be less than 200 L).

Precipitates and Proteins of Interest

Many different methods can be used to selectively precipitate proteins from solution, for instance by the addition of salts, alcohols and/or polyethylene glycol with the combination of pH adjustment and/or a cooling step. It is therefore anticipated that the present invention will be applicable to most protein precipitates, such as immunoglobulin G-containing protein precipitates, regardless of how they are initially prepared. It should be noted that the present invention can also be implemented in separating other types of protein including albumin, immunoglobulins (Ig), such as IgA, IgD, IgE or IgM, either each type of immunoglobulin alone or a mixture thereof. It is foreseen that recombinant proteins are also suitable in this regard.

To this end, it is noted that, if the method is applied to producing IgG, the protein-comprising precipitate can be any IgG-containing material (e.g. in form of a paste, precipitate, or inclusion bodies) or derived from a starting material such as a solution from which the IgG can be precipitated by for example one or more of the methods explained above, whether from plasma or serum of human or animal origin, fermentation broth, cell culture, protein suspension, milk or other original sources. The immunoglobulin-containing material or solution may contain monoclonal or polyclonal immunoglobulin(s). In some embodiments, the immunoglobulin-containing starting material is a solution comprising polyclonal antibodies. In other embodiments the starting material comprises a monoclonal antibody or a fragment thereof. It is therefore within the knowledge of a skilled person that the term "immunoglobulin" as used herein can also be identified as antibody including monoclonal antibody or polyclonal antibody, either natural or recombinant.

For instance, the immunoglobulins (e.g. IgG) can be isolated from human or animal blood or produced by other means such as by recombinant DNA technology or hybridoma technology. In preferred embodiments, immunoglobulins are obtained from blood plasma, typically from a pool of blood plasma derived from many donors. In order to obtain the immunoglobulins from plasma, the plasma is usually subjected to alcohol fractionation, which may be combined with other purification techniques like chromatography, adsorption or precipitation. However, other processes can also be used. For instance, the protein-comprising precipitate can be the II+III precipitate according to the Cohn's methods such as the Method 6, Cohn et. al. J. Am; Chem. Soc., 68 (3), 459-475 (1946), the Method 9, Oncley et al. J. Am; Chem. Soc., 71, 541-550 (1946), or the I+II+III precipitate, the Method 10, Cohn et. al. J. Am; Chem. Soc., 72, 465-474 (1950); as well as the Method of Deutsch et. al. J. Biol. Chem. 164, 109-118 (1946) or the Precipitate-A of Nitschmann and Kistler Vox Sang. 7, 414-424 (1962); Helv. Chim. Acta 37, 866-873 (1954). Alternative precipitates comprising the protein of interest include but are not limited to other immunoglobulin G-containing Oncley fractions, Cohn fractions, ammonium sulphate precipitates from plasma described by Schulze et al. in U.S. Pat. No. 3,301, 842. Further alternative precipitates comprising the protein of interest include but are not limited to octanoic acid precipitates, as described, for example, in EP0893450.

"Normal plasma", "hyperimmune plasma" (such as hyperimmune anti-D, tetanus or hepatitis B plasma) or any plasma equivalent thereto can be used as a starting material in the cold ethanol fractionation processes described herein.

The term rcryosupernatant' (also called cryo-poor plasma, cryoprecipitate depleted plasma and similar) refers to plasma (derived from either whole blood donations or plasmapheresis) from which the cryoprecipitate has been removed. Cryoprecipitation is the first step in most plasma protein fractionation methods in use today, for the large-scale production of plasma protein therapeutics. The method generally involves pooling frozen plasma that is thawed under controlled conditions (e.g. at or below 6° C.) and the precipitate is then collected by either filtration or centrifugation. The supernatant fraction, known to those skilled in the art as a "cryosupernatant", is generally retained for use. The resulting cryo-poor plasma has reduced levels of Factor VIII (FVIII), von Willebrand factor (VWF), Factor XIII (FXIII), fibronectin and fibrinogen. While the levels of FVIII are greatly reduced, levels of fibrinogen can be as much as 70% of original levels. Cryosupernatant provides a common feedstock used to manufacture a range of therapeutic proteins, including alpha 1-antitrypsin (AAT), apolipoprotein A-I (APO), fibrinogen, antithrombin III (ATM), prothrombin complex comprising the coagulation factors (II, VII, IX and X), albumin (ALB) and immunoglobulins such as immunoglobulin G (IgG).

The supernatant of the 8% ethanol-precipitate (method of Cohn et al.; Schultze et al. (see above), p. 251), precipitate II+III (method of Oncley et al.; Schultze et al. (see above) p. 253) or precipitate B (method of Kistler and Nitschmann; Schultze et al. (see Schultze above), p. 253) are examples of a source of IgG compatible with industrial scale plasma fractionation. The starting material for a purification process to gain IgG in high yield can alternatively be any other suitable material from different sources like fermentation and cell culture or other protein suspensions.

In the Cohn fractionation method, the first fractionation step results in fraction I which comprises mainly fibrinogen and fibronectin. The supernatant from this step is further processed to precipitate out fraction II+III and then fractions III and II. Typically, fraction II+III contains approximately 60% IgG, together with impurities such as fibrinogen, IgM, and IgA. Most of these impurities are then removed in fraction III, which is considered a waste fraction and is normally discarded. The supernatant is then treated to precipitate out the main IgG-containing fraction, fraction II, which can contain greater than 90% IgG. The above % values refer to % purity of the IgG. Purity can be measured by any method known in the art, such as gel electrophoresis or immune-nephelometry. In the Kistler & Nitschmann method, fraction I is equivalent to fraction I of the Cohn method. The next precipitate/fraction is referred to as precipitate A (fraction A). This precipitate is broadly equivalent, although not identical, to Cohn fraction II+III. The precipitate is then redissolved and conditions adjusted to precipitate out precipitate B (fraction B), which is equivalent to Cohn fraction III. Again, this is considered to be a waste fraction, and is normally discarded. The precipitate B supernatant is then processed further to produce precipitate II, which corresponds to Cohn Fraction II.

Particular protein-comprising precipitates can comprise plasma proteins, peptide hormones, growth factors, cytokines and polyclonal immunoglobulins proteins, plasma proteins selected from human and animal blood clotting factors including fibrinogen, prothrombin, thrombin, prothrombin complex, FX, FXa, FIX, FIXa, FVII, FVIIa, FXI, FXIa, FXII, FXIIa, FXIII and FXIIIa, von Willebrand factor, transport proteins including albumin, transferrin, ceruloplasmin, haptoglobin, hemoglobulin and hemopexin, protease inhibitors including β-antithrombin, α-antithrombin, α-2-macroglobulin, C1-inhibitor, tissue factor pathway inhibitor (TFPI), heparin cofactor II, protein C inhibitor (PAI-3), Protein C and Protein S, α-1 esterase inhibitor proteins, α-1 antitrypsin, antiangionetic proteins including latent-antithrombin, highly glycosylated proteins including α-1-acid glycoprotein, antichymotrypsin, inter-α-trypsin inhibitor, α-2-HS glycoprotein and C-reactive protein and other proteins including histidine-rich glycoprotein, mannan binding lectin, C4-binding protein, fibronectin, GC-globulin, plasminogen, blood factors such as erythropoietin, interferon, tumor factors, tPA, γCSF.

In particular embodiments the protein-comprising precipitate is used in the manufacture of therapeutic proteins derived from plasma including immunoglobulins such as immunoglobulin G, albumin, fibrin, thrombin, prothrombin complex, fibrinogen, plasminogen, alpha 1-antitrypsin, C1-inhibitor, apolipoprotein A1, alpha acid glycoprotein, haptoglobin, hemopexin, transferrin and coagulation factors such as Factor VII, Factor VIII and Factor IX.

Dynamic Filter Element

In any aspect of the present invention, the dynamic filter element filtration unit adapted for removing impurities from the first suspension and or for removing precipitant from the second suspension, is a dynamic cross flow filter element. In a preferred embodiment the dynamic cross flow filter element is a rotational cross flow filter element. More preferably the rotational cross flow filter element comprises a filter disc. The filter discs are usually mounted on a shaft member. In an embodiment the rotational cross flow filter element comprises at least one filter disc and at least one shaft member.

According to a preferred embodiment of any aspect of the present invention, the filter disc membrane is a ceramic membrane. More preferably the ceramic membrane has a pore size in the range of greater than or equal to 5 nm to less than or equal to 2 μm. In particular embodiments, the ceramic membrane has a pore size of from about 0.2 μm to 2 μm. In particular embodiments, the ceramic filter membrane has an average pore size in the range of greater than or equal to 5 nm to less than or equal to 200 nm (0.2 μm). In particular embodiments, the ceramic filter membrane has an average pore size in the range of greater than or equal to 50 nm to less than or equal to 100 nm. Such filter discs are supplied by Kerafol and Flowserve.

It will be understood that a plurality of filter disc membranes can be included in the dynamic filter element filtration unit adapted for removing impurities from the first suspension and or for removing precipitant from the second suspension. As such, the present methods contemplate the use of one, two, three, four, five, six or more filter disc membranes for removing impurities from the first suspension and or for removing precipitant from the second suspension. The plurality of filter disc membranes may have pore sizes that are the same or different.

The filtration unit adapted for removing impurities from the first suspension and or for removing precipitant from the second suspension, in preferred embodiments comprises a pressure vessel. The suspension from the first tank can be continuously fed into the pressure vessel via an inlet port. An even distribution of the suspension in the vessel can be achieved using a distribution manifold. Hence in particular embodiments the pressure vessel comprises a distribution manifold. In some embodiments the first filtration unit comprises a rotational cross flow filter element. Preferably the filter element contains more than one filter disc evenly spaced along at least one hollow central collection shaft. The filter discs can be arranged either horizontally or vertically. When in the horizontal orientation they are spaced along a vertically orientated hollow collection shaft. The collection shaft and discs are rotatable. The suspension in the pressure vessel can then penetrate the outer membrane of the rotating filter discs so as to pass through into a hollow central portion of the disc which is in turn channeled into the central collection shaft. Typically, the filtrate (i.e. the first permeate enriched in the protein of interest) can then be removed from the shaft portion of the first filtration unit via a flanged port. Whilst the retentate remaining in the pressure housing can be fed out of the vessel via an outlet port. Generally, the retentate is recirculated to the first tank to dilute the suspension. In this way, the retentate from the first filtration unit can be utilised to dilute the suspension in the first tank to a second dilution factor.

Dynamic cross flow filtration such as rotational filtration provides maximum filter efficiency. The cross flow effect (tangential flow cleaning of the filter surface) is generated by rotating the filter discs and not by pumping large volumes across a fixed membrane as used in conventional (static) cross flow filtration systems. The extreme cross flow velocities generated at the surfaces of the rotating filter discs ensure a highly efficient cleaning of the filter surface, whilst consuming very low amounts of energy compared to conventional cross flow techniques.

Dynamic filter elements can also be employed in the third filtration unit of the first aspect of the invention, and/or the second or fourth filtration units of the second aspect of the invention, in other words, to perform the continuous concentration process. Such dynamic filter elements will typically comprise one or more ultrafiltration or diafiltration membranes.

The cross flow filter element for performing the continuous concentration process may include a dynamic ultrafiltration filter device. Alternatively, the process comprises a static ultrafiltration device.

In preferred embodiments of the invention the dynamic cross flow filter element or the ultrafiltration filter device for performing the concentration process comprises a membrane with a molecular weight cutoff less than the molecular weight of the protein of interest. In these embodiments the membrane cutoff is selected to retain the protein of interest during the concentration process. As a general guide a nominal membrane cutoff at least 3-fold lower than the molecular weight of the protein of interest can be selected to ensure the protein is retained in the retentate.

In one alternative embodiment the dynamic cross flow filter element or the static ultrafiltration filter element for performing the concentration process comprises a membrane with a molecular weight cutoff greater than the molecular weight of the protein of interest. In such embodiments the nominal membrane cutoff is selected to ensure the protein of interest passes across the membrane and is collected in the second or fourth permeates rather than the second or fourth retentates (in the case of the second aspect of the invention) or in the third permeate rather than third retentate (in the case of the first aspect of the invention).

In embodiments where the cross flow filter element is dynamic, preferably the element is a rotational cross flow filter element, adapted for performing a continuous concentration process.

According to a further preferred embodiment, the filtration element for performing the continuous concentration process comprises a filtration membrane having an average pore size of between 5 nm to 5000 nm, preferably between 5 nm to 2000 nm, between 5 nm to 1000 nm, between 5 nm to 500 nm, between 5 nm to 200 nm, between 7 nm to 1000 nm, more preferably between 7 nm to 500 nm, even more preferably between 7 nm to 100 nm, most preferably between 7 nm to 80 nm. Of course, the average pore size can be in other combinations of the range given above. Filter manufacturers often assign terms like nominal or mean pore size ratings to commercial filters, which usually indicate meeting certain retention criteria for particles or microorganisms rather than the geometrical size of the actual pores.

In a particular embodiment the rotational cross flow filter element for performing the continuous concentration process comprises a filter disc (such as a ceramic disc). In some embodiments the filter disc comprises a membrane with an average pore size of a microfilter. In other embodiments the filter disc comprises a membrane with an average pore size of an ultrafilter. In further embodiments, the filter disc comprises a membrane with an average pore size of a diafilter. In an embodiment the average pore size of the filter disc membrane is in a range from greater than or equal to 5 nm to less than or equal to 2 μm. In particular embodiments the average pore size of the filter disc membrane is in a range from greater than or equal to 50 nm to less than or equal to 500 nm (i.e. 0.5 μm). In some embodiments the filter disc membrane has an average pore size in the range of greater than or equal to 50 nm to less than or equal to 100 nm, or in the range of greater than or equal to 60 nm to less than or equal to 90 nm, or in the range of greater than or equal to 60 nm to less than or equal to 80 nm. In some embodiments, the filter disc membrane has an average pore size of 60 nm or 80 nm.

In particularly preferred embodiments, the rotational cross flow filter element for performing the continuous concentration process comprises a plurality of ceramic discs with a pore size suitable for ultrafiltration and/or diafiltration. For example, the element preferably comprises at least one ceramic membrane having a pore size of 3 nm. Alternatively, the element preferably comprises at least one ceramic membrane having a pore size of 5 nm. Alternatively, the element preferably comprises at least one ceramic membrane having a pore size of 7 nm. Alternatively, the element preferably comprises at least one ceramic membrane having a pore size of 30 nm. The element may comprise a plurality of ceramic discs with varying pore sizes, including wherein the pore sizes are 3 nm and 5 nm. The element may comprise a plurality of ceramic discs with varying pore sizes, including wherein the pore sizes are 5 nm and 7 nm. The element may comprise a plurality of ceramic discs with varying pore sizes, including wherein the pore sizes are 3 nm and 30 nm. The element may comprise a plurality of ceramic discs with varying pore sizes, including wherein the pore sizes are 3 nm, 5 nm, 7 nm and 30 nm.

According to yet a further preferred embodiment, a filtration element for performing the continuous concentration process comprises an ultrafiltration device comprising a membrane in the form of a polymer membrane, such as polyethersulfone or regenerated cellulose.

Protein Recovery

The concentration of protein(s) in a sample (e.g., in the supernatant or a subsequently purified preparation thereof) can be measured by any means known to persons skilled in the art. Examples of suitable assays include high pressure liquid chromatography (HPLC; e.g., size exclusion HPLC), enzyme-linked immunosorbent assay (ELISA) and immunonephelometry. Such techniques can be used to assess purity of a sample. In addition, gel electrophoresis like SDS-PAGE with staining and densitometry may be used to assess purity of the sample and detect the presence of contaminating proteins. A reducing agent such as dithiothreitol can be used with SDS-PAGE to cleave any disulfide-linked polymers.

The immunoglobulin G-containing starting material preferably has a total protein concentration of about 0.5 to 6.5% w/v, more preferably about 1.0 to 4.0% w/v, still more preferably about 1.5 to 3.0% w/v, most preferably about 1.8 to 2.5% w/v, e.g. about 2.0% w/v.

In one embodiment, the liquid comprises a buffer comprising one of more of sodium acetate, phosphate and citric acid. In one embodiment, the phosphate is a sodium phosphate, such as sodium dihydrogen phosphate dehydrate. Preferably, a buffer with low conductivity is used, such as a buffer with a conductivity below 5 mS/cm, preferably below 4 mS/cm, more preferably between 0.01 mS/cm to 4 mS/cm.

In any embodiment, the temperature at which conductivity of a solution is measured can be between about 4° C. and 37° C., preferably, wherein the temperature is between about 20-25° C. (room temperature).

The method according to the present invention allows the protein of interest to be recovered in a high yield from the protein-comprising precipitate (e.g. paste). The recovered yield (ultrafiltered product), in post concentration stage, is typically at least 75% (w/w), at least 80% (w/w), at least 85% (w/w), at least 90% (w/w), at least 95% (w/w), preferably at least 96% (w/w), more preferably at least 97% (w/w), most preferably up to 98% (w/w), defined as the total amount of immunoglobulin G in the final filtered solution compared to the total amount of immunoglobulin G in the starting material.

The following is an example demonstrating how the calculation of the recovery rate of the immunoglobulin G content can be obtained according to the present invention. A first step involves the determination of the IgG content in the starting material (i.e., the protein-comprising precipitate; total dissolution) followed by a second step which involves the determination of the IgG recovery obtained when the continuous extraction method or system of the present invention is used.

As a first step, the protein-comprising precipitate (about 50 g for each experiment) is dissolved in a buffer (e.g., 0.12 M to 0.25 M phosphate buffer, pH 7.6 to 8.0) to give a final dilution factor of 20 (1:20; or a final dilution ratio of 1:19 by weight). After a resuspension duration of 2 h using an impeller mixer, the suspension is centrifuged at 4500 G. This results in a first supernatant and a first precipitate. The volume of supernatant can be determined by standard methods, and the IgG content of the supernatant can be determined, for example, by nephelometry. The resulting precipitate is resuspended and treated again using the same buffer as described above to give a final dilution factor of 20 (1 part of supernatant obtained:19 parts of new buffer). The volume of the resulting supernatant and IgG content is determined again. This process is repeated for example five times, or as often as necessary so that the IgG content in the last supernatant is below 10 mg/L (quantification limit is approximately about 3.6 mg/L). This procedure ensures that the IgG content in the protein-comprising precipitate is completely or optimally dissolved or extracted by the buffer. This experiment is repeated several times (12 individual experiments were repeated in the present case). This process was repeated with different starting precipitates generated from fractionation of source plasma which gave similar reliable results. Table 1 below shows the content of the total protein and IgG recovered from the protein-comprising precipitate.

TABLE 1

| Determination of the IgG content in the protein-comprising precipitate (total dissolution). | | | |
|---|---|---|---|
| | accumulative dilution factor (paste:buffer) weight:weight | Recovery total protein (g/kg paste) (min-max) | Recovery IgG (g/kg paste) (min-max) |
| After 1$^{st}$ extraction | 1:20 | 131.8-158.9 | 68.7-72.8 |
| After 2$^{nd}$ extraction | 1:40 | 16.2-23.1 | 7.1-10.5 |
| After 3$^{rd}$ extraction | 1:60 | 3.5-7.4 | 0.6-1.8 |
| After 4$^{th}$ extraction | 1:80 | 1.1-2.3 | 0.05-0.2 |
| After 5$^{th}$ extraction | 1:100 | 0.2-0.4 | 0.01-0.03 |
| Total extraction | | 152.8-192.1 | 76.5-85.3 |

In the second step, the same protein-comprising precipitate is used for an experiment that employs the continuous extraction and separation method or system according to the present invention. A total amount of 1 kg of the protein-comprising precipitate (Precipitate A) is dissolved in the buffer (e.g. 10 mM phosphate, 10 mM acetate & 2 mM citric acid) for 30 minutes to give a starting suspension with a first dilution ratio of 5 (1:6 by weight; or equal to a first dilution factor of 6 (1:6)). The pH of the suspension is 4.6. The suspension is transferred from a first tank into a first filtration process unit for a continuous extraction and separation process. For each 100 to 200 ml collected filtrate, 100 to 200 ml of fresh buffer (or recirculated buffer (i.e. second permeate) after the UF step) is added to the first tank such that the volume of the filtered suspension remains constant in the first tank. The filtration is terminated after 4 hours, whereby the total protein concentration in the suspension is expected to be below 0.1 g/L and/or the IgG concentration is below 50 mg/L.

The following Table 2 shows the recovery rate of the IgG.

TABLE 2

Determination of the IgG recovery using the continuous extraction filtration system of the present invention

| Starting precipitate used | Precipitate A |
|---|---|
| Amount of starting precipitate (kg) | 1.0 |
| First dilution factor (paste: total by weight) | 1:6 |
| Total protein amount (at the first dilution factor) (g/kg paste) | 116.4 |
| IgG amount (at the first dilution factor) (g/kg paste) | 61.7 |
| Final dilution factor (end of the continuous extraction & filtration) | 1:31 |
| Total protein amount (after reaching the final dilution factor) (g/kg paste) | 168 |
| IgG amount (after reaching the final dilution factor) (g/kg paste) | 78.9 |
| IgG amount (post ultra-filtration) (g/kg paste) | 78.6 |

In this example, the experiment is performed off-line to show the increased yield of total protein and IgG using the continuous extraction filtration unit. "Off-line" means that the buffer added is not obtained from a second filtration unit. Ultrafiltration in the second filtration unit is carried out separately. Also it is shown in Table 2 that the IgG amount is lower at the first dilution factor (1:6=61.7 g/kg) compared to the IgG amount at the end of the final (second) dilution factor (1:31=78.9 g/kg). This is due to the fact that not all IgG is extracted or dissolved in the buffer at once but rather is extracted or dissolved over a period or a repetitive dissolving procedure. Hence, the IgG yield is increased through the continuous extraction and filtration process according to the present invention.

The yield of the immunoglobulin G according to the present invention with a recovery rate of at least 95% is achieved, as shown by Tables 1 and 2 above. The recovery rate (of the continuous extraction and filtration according to the present invention) is calculated by the ratio (of total amount of IgG in continuous filtrate:average amount of IgG by total dissolution from Table 1) multiplied by 100.

Total IgG amount (after reaching the final dilution factor)=78.9 g/kg

Average total IgG extraction (Table 1)=(76.5+85.3)/2=80.9 g/kg

Yield of IgG (Recovery rate)=78.9/80.9×100%=97.53%

Hence, it is shown herewith that at least 95% or approximately 98% of IgG recovery rate according to the present invention can be achieved.

High recovery at this early process step (before further downstream processing steps) is a prerequisite to achieve higher yields at the final bulk stage. The present invention utilizes the extraction process, wherein protein-comprising precipitate (e.g. paste) is in effect suspended with a high dilution factor (e.g. between 40 and 70; 1:40 and 1:70). As an example, 1 kg of protein-comprising precipitate (e.g. paste) is resuspended in 3 kg of liquid (e.g. buffer), resulting in a starting suspension with a first dilution factor of 4 (1:4). Recirculation of 66 kg of the feedstream of buffer results in a final dilution factor of 70 (1:70). The extraction process used in the present invention allows higher amounts of immunoglobulin G to be released into the suspension/solution, thus shifting the equilibrium (as will be discussed below), allowing for a more efficient separation of immunoglobulin G from the suspension.

In a preferred embodiment, the crude immunoglobulin G-containing protein precipitate (i.e. the protein-comprising precipitate) is suspended in a buffer to yield the starting suspension. The buffer may in some embodiments contain acetate or phosphate, or additionally citric acid.

In the most preferred embodiment, the extracted and filtered product of immunoglobulin G enriched suspension or solution comprises human immunoglobulin, wherein at least 95% or up to 98% immunoglobulin G content is recovered from the starting precipitate, or less than 0.1 mg/ml, preferably less than 0.05 mg/ml of immunoglobulin G protein concentration can be detected in final suspension after the second dilution factor has been reached. The approximate distribution of the immunoglobulin G subclasses will typically resemble about the average subclass distribution in human plasma.

Moreover, typically 1 kg of Precipitate A (protein-comprising precipitate) contains around 170 g of total protein (range: 150-190 g protein/kg precipitate). The total protein is made up of approximately 50% to 60% of IgG (thus ranging between 75-95 g/kg precipitate). According to the one method of the present invention, when a recovery rate of approximately 98% of IgG is achieved, that means a total amount of 73.5-93.1 g/kg of IgG are obtained from the protein-comprising precipitate (Precipitate A).

The above method for calculating percentage IgG recovery can be further applied to the present invention, including by collecting the first filtrate in a second tank prior to precipitation and further subsequent continuous extraction and separation.

In chemistry for instance in protein separation, Le Chatelier's principle or "The Equilibrium Law" can be used to predict the effect of a change in conditions on a chemical equilibrium. When any system at equilibrium is subjected to change in concentration, temperature, volume, or pressure, then the system readjusts itself to counteract (partially) the effect of the applied change and a new equilibrium is established. In other words, whenever a system in equilibrium is disturbed the system will adjust itself in such a way that the effect of the change will be nullified. For instance, at equilibrium, the concentrations of immunoglobulin in suspension on either side are constant. If at equilibrium a small amount of the immunoglobulin is taken out from the reaction, due to the changing of the immunoglobulin concentration, this will shift the equilibrium to the side that would reduce that change in concentration. According to Le Chatelier's principle the system will attempt to partially oppose the change affected to the original state of equilibrium. In turn, the rate of reaction, extent and yield of products will be altered corresponding to the impact on the system.

If a system is at equilibrium and the concentration of one of the species involved in the reaction is increased, the system will readjust so as to decrease the concentration of that species. Thus, the reaction will proceed in such a manner so as to consume some of the increased concentration. Similarly, if the concentration of some substance is decreased, the reaction will proceed so as to make up the loss in the concentration.

In other words, under constant removal of immunoglobulin (e.g. IgG) from the system and at the same time, reducing the concentration of immunoglobulin in the solvent of the suspension through dilution, this leads to the increase of removing immunoglobulin from one phase of the suspension, i.e. the precipitate to the liquid phase. Through repetition of this procedure essentially all immunoglobulin included in the precipitate of the suspension can be extracted from the protein-comprising precipitate, in particular present invention discloses a high final dilution factor of at least 30, preferably e.g. 40 (1:40) or higher, and can be further assisted by using for example the proposed buffer compositions, or additionally assisted by using a higher pH to maximise immunoglobulin G recovery from the protein-comprising precipitate. Compared to the prior art, the method and system of the present invention allows almost all immunoglobulin G to be recovered from the protein-comprising precipitate (e.g. paste or precipitate).

The ultrafiltered product can later be subjected to further processing such as chromatography steps, virus inactivation steps, concentration and formulation so that the end product can be administered for example to the human body. The end product can be used in the treatment of immune conditions, particular autoimmune diseases and certain neurological diseases. These conditions include Rheumatoid arthritis, Systemic Lupus Erythematosus (SLE), Antiphospholipid syndrome, immune thrombocytopenia (ITP), Kawasaki disease, Guillain Barre syndrome (GBS), multiple sclerosis (MS), chronic inflammatory demyelinating polyneuropathy (CIDP), multifocal motor neuropathy (MMN), myasthenia gravis (MG), skin blistering diseases, scleroderma, Dermatomyositis, Polymyositis, Alzheimer's Disease, Parkinson's Disease, Alzheimer's Disease related to Downs Syndrome, cerebral amyloid angiopathy, Dementia with Lewy bodies, Fronto-temporal lobar degeneration or vascular dementia. In addition, the end IVIg and SCIg products can be used in other medical procedures such as in cell and organ transplant.

To this end, it is reiterated that the first process unit according to the present invention (and/or the third process unit according to the second aspect of the invention) provides a continuous extraction and separation process, in particular a filtration process, thanks to its unique design. The first process unit may be provided with a dynamic rotation filtration element, for example comprising a ceramic-based membrane disc. The rotation filtration allows extreme cross flow velocity (due to its highly efficient cleaning of the filter surface) and has a very low energy consumption compared to conventional cross flow techniques. A cross flow effect (tangentially flow cleaning of the filter surface) is generated by the rotating of the filter discs and not by pumping of large volumes. The ceramic filter disc has better resistance to chemical and thermal stresses, high filtration flux and very long service life, and can be regenerated by backflushing or hot steam sterilization.

Dynamic Cross Flow Filtration Unit and System

Dynamic cross flow filtration such as rotational filtration provides maximum filter efficiency. The cross flow effect (tangential flow cleaning of the filter surface) is generated by rotating the filter discs and not by pumping large volumes across a fixed membrane as used in conventional (static) cross flow filtration systems. The extreme cross flow velocities generated at the surfaces of the rotating filter discs ensure a highly efficient cleaning of the filter surface, whilst consuming very low amounts of energy compared to conventional cross flow techniques.

In the dynamic cross flow filtration units and systems of the invention, the rotating ceramic filter discs are typically assembled in a pressurised housing. The design of the discs shows drainage channels in the inside. The filtrate is transported from the outside to the inside of the discs. The rotation of the discs generates shear forces on the membrane surface. With this technique an increase of a filter cake is avoided resulting in a high filtration flux. Some of main parameters of the rotation filtration is the rotation speed for rotating the ceramic filter disc and solid content (concentration of liquids due to the removal of filtrate).

The temperature has an effect on the viscosity of a protein solution and therefore also has an effect on the flux upon filtration with a membrane. The starting suspension to be used in the method of the invention will preferably have a temperature within the range from 0° C. up to the temperature at which the protein concerned is denatured. The temperature is typically within the range of from about 10° C. up to about 50° C. In particular embodiments the temperature is within the range of from about 18° C. up to about 35° C. According to one preferred embodiment, the temperature of the second suspension tank (i.e., the tank comprising the fatty acid, preferably caprylic (octanoic) acid for precipitating one or more impurities in the first permeate of the first aspect of the invention or the second retentate of the second aspect of the invention, both enriched for the protein of interest) is at a temperature of between about 4° C. to about 40° C. More preferably, the fatty acid, preferably caprylic (octanoic) acid is combined with the first permeate of the first aspect of the invention or second retentate of the second aspect of the invention, in the second suspension tank at a temperature of between about 25° C. to about 38° C., optionally about 27° C., about 32° C. or about 37° C. Optionally, both the permeate or retentate enriched for the protein of interest and the fatty acid are at a temperature of between about 4° C. to about 40° C., preferably about 25° C. to about 38° C., more preferably about 32° C. when they are combined. In other words, while the permeate may be circulating in the filter units at one temperature, the temperature of the permeate may be increased prior to and/or during the period of incubation with the fatty acid in the second suspension tank.

According to a further preferred embodiment, the temperature in the filter units is controlled, preferably between 2° C. and 25° C., more preferably at about 2° C. to 10° C. Such temperature ensures an optimum extraction process and separation process while maintaining the bio-reactivity of the protein of interest throughout the processes.

Filtration is performed with a transmembrane filtration pressure that is the same as or below the level at which the membrane can withstand, depending on the material of the membrane to be used herein, for example with pressures of about 0.2 to about 3 bar. The transmembrane pressure is typically from 0.1 to 2.5 bar, preferably from 0.2 to 2.4 bar, more preferably from 0.4 to 2.0 bar, from 0.5 to 1.8 bar, from 0.6 to 1.6 bar, from 0.6 to 1.5 bar, from 0.7 to 1.5 bar, most preferably from 0.8 to 1.5 bar. According to another embodiment, a pressure of up to 2 bar, preferably between 0.1 to 2.0 bar, or about 1.5 bar, 1.0 bar or 0.5 bar is provided to filter units.

According to another embodiment, the continuous extraction process in the filter units adapted to separate impurities/precipitant from the first and second suspensions, is further assisted by regulating the flow rate and/or the residence time of the suspension or the solution into the filter units and/or the flow rate of the retentate/raffinate comprising impurities/precipitant and/or the flow rate of the first permeate/filtrate enriched for the protein of interest. For instance, in one embodiment, the linear velocity of the suspension or the solution into the pressure vessel (filtration process unit) can be about 0.27 to 1.66 m/s. In another example, the linear velocity of the retentate comprising impurities/precipitant can be 0.25 to 1.33 m/s. In another example, the linear velocity of the permeate/filtrate enriched for the protein of interest can be 0.03 to 0.33 m/s. Linear velocity multiplied by the cross-sectional area gives the volumetric flow rate. In addition, a turbulence can be created in the first process unit as a result of the speed of the rotating filter discs, wherein the speed (sometimes referred to as tangential speed) can be between about 1 to 7 m/s. According to an embodiment of the present invention, the speed of the rotating disc filters is between 1 to 10 m/s. In a preferred embodiment of the present invention, the speed of the rotating disc filters is between 5 to 7 m/s. More preferably the speed of the rotating disc filters is 7 m/s at 60 Hertz (800 rpm). The rotating speed of the rotational cross-filter element is between about 600 rpm (50 Hz) and about 1600 rpm (100 Hz), preferably between about 800 rpm (60 Hz) and about 1200 rpm (80 Hz), preferably about 800 rpm (60 Hz), about 1000 rpm (70 Hz) or about 1200 rpm (80 Hz). As used herein, the rotating speed in Hz is intended to refer to the speed of the motor. This can be correlated with the speed in rpm using an appropriate calibration curve.

This method allows a continuous extraction and a separation process to be realised for maximising the recovery of the protein of interest from the starting precipitate/material (i.e., the first suspension) or from the second suspension. Thanks to the extraction process, almost all the protein of interest is extracted from the protein-comprising precipitate and is recovered in subsequent stages. This method also allows the liquid or diluent e.g. buffer or water to be re-circulated in a closed system and hence the quantity of the liquid is maintained throughout the process while footprints (i.e. large tank volume) can be reduced.

In still further embodiments, the present invention includes a step of backflushing in conjunction with dynamic crossflow filtration, in order to flush contaminants that may have built up in the system. Typically, the methods and systems of the invention include alternating filtration and backflushing such that the filtration is temporarily paused (i.e., the feed pump is stopped) while a period of backflushing occurs, at regular intervals. where the flow of liquid into the filtration system is reversed, It will be understood that the frequency, duration and flow rate of the backflushing can be adjusted in order to maximize filtration efficiency and the period of filtration before backflushing is required.

In certain preferred embodiments, the frequency of backflushing (and consequently, the period of filtration) is determined based on the total protein concentration or the number of impurities in the starting material. Consequently, it will be appreciated that backflushing will be required more frequently when filtering the first suspension compared to when the second suspension (which has relatively fewer impurities) is being filtered. In other words, as the total protein concentration and turbidity of the filtrate decreases, the frequency of the backflushing interval will also decrease (i.e. the period of time between backflushes increases and filtration can proceed for a longer period of time before a backflush is required).

Protein concentration and turbidity of the filtrate can be monitored by various methods known in the art. In certain embodiments, the methods of the invention and systems of the invention include the use of an in-line detection unit that enables measurement of protein concentration and/or turbidity as the filtrate passes into and/or out of the filtration unit. In further embodiments, a dual wavelength photometer can be employed to facilitate simultaneous assessment of protein concentration (e.g., by detecting absorbance of the solution at a wavelength suitable to detecting protein concentration, such as in the range of 260-280 nm, preferably about 280 nm) and solution turbidity (e.g., by detecting absorbance of the solution at a wavelength suitable for detecting light scattering caused by the presence of particulate matter, such as absorbance at a wavelength in the range of 400 nm to 900 nm, preferably about 600 nm to about 880 nm). Dual wavelength photometric devices for use in conjunction with chromatographic and filtration units are well known in the art.

In certain examples, the frequency of backflushing is at 15 second intervals, 30 second, 45 second, 60 second, 75 second, 90 second, 105 second, 120 second, 135 second, 150 second, 200 second, 230 second, 260 second, 300 second, 330 second, 360 second, 400 second, 1000 second, 2000 second, 3000 second, 4000 second or greater intervals.

It will be appreciated that the duration of the backflushing interval will vary with the filtration area and number of discs requiring backflushing. The larger the filtration area, typically, the larger the volume of backflushing buffer that is required and therefore the duration of the backflushing will also be dictated by the flow rate during backflushing. The skilled person will be well able to determine suitable duration, frequency, and flow rates for backflushing, depending on the size of the system and number of discs being employed. In certain examples, the duration of backflushing is approximately 5 seconds, approximately 10 seconds, approximately 15 seconds, approximately 30 seconds, approximately 45 seconds, approximately 60 seconds, or longer.

It will be appreciated that for practical reasons (and to maximize filtration efficiency) the duration of the backflushing interval is typically less than the duration of the filtration interval. In certain embodiments, the duration of the backflushing interval is at least one quarter, one eighth, one tenth, one sixteenth or smaller than the duration of the filtration interval.

It will further be appreciated that the flow rate that is used during backflushing may be the same or different to the flow rate used for filtration. In certain embodiments, the flow rate during dynamic filtration is in the range of approximately 15 to 100 L/hour, preferably in the range of about 20 to 50 L/hour (about 200 ml/min to about 1 L/min, preferably about 300 to about 900 ml/min, more preferably about 300 to 600 ml/min). Preferably the flow rate of backflushing is lower than the flow rate used for filtration such that in certain embodiments, the flow rate of backflushing is in the range of about 100 to about 400 times slower than the flow rate used for filtration.

In certain embodiment, the backflushing is performed with the same buffer comprised in the first or second suspensions. Alternatively, the backflushing may be performed using the permeate that is obtained during the concentration process (e.g., when using ultrafiltration coupled to dynamic cross flow filtration to concentrate the filtrate obtained from dynamic cross flow filtration).

EXAMPLES

Example 1

Process Step 1

The starting material used to prepare the first suspension is either Precipitate I+II+III or Precipitate A. An optimal filtration is defined by the retention of filter aid in the suspension while IgG is fully extracted from the paste and recovered in the filtrate in the shortest amount of time. Process 1 results in a filtrate that is filter aid-free. However, impurities such as IgA, IgM, and albumin will still be present. These will be removed to a great extent using octanoic acid (OA) in Process Step 2.

The starting material is resuspended in the desired buffer (1:5) using an impeller mixer and then transferred to tank 1 (the suspension tank). The suspension is pumped to the first processing unit to start the continuous extraction (CE) process. The unfiltered suspension returns to the suspension tank as retentate. This circulation is maintained while solubilized proteins are filtered across the ceramic discs. The filtrate containing IgG and various impurities is collected in a second tank (filtrate tank). When a defined volume in the second tank is reached, the concentration process is started using systems 2 and 3 (comprising ultrafiltration and diafiltration membranes). The transmembrane pressure (TMP) is regulated to ensure that the combined permeate flow from systems 2 and 3 equals the filtrate flow from system 1, ensuring a constant volume in the suspension tank during the extraction process. The filtration unit is stopped once the protein concentration in the filtrate is below a defined threshold. At this time point, the final dilution ratio of ≥1:25 is reached. The concentration is continued until the protein concentration in the collection tank reaches 17-20 g/L. During this final concentration, the permeate flows to waste.

Process Step 2

The first concentrate comprising IgG (filtrate/concentrate) is transferred to a tank where OA treatment is to take place. This can be the same tank used for suspension of the starting material (i.e., the suspension tank) but after the tank has been cleaned. After addition of OA to the concentrated protein, the OA-suspension is recirculated over system 1 in order to enable excellent dispersion of OA and excellent extraction of IgG. The OA-suspension is pumped to the first processing unit to start the continuous extraction process. The unfiltered suspension returns to the suspension tank as retentate. This circulation is maintained while IgG is filtered across the ceramic discs. The OA-filtrate comprising IgG is collected in a second tank (filtrate tank). When a defined volume in the second tank is reached, the concentration process is started using systems 2 and 3 (comprising ultrafiltration and diafiltration membranes). The transmembrane pressure (TMP) is regulated to ensure that the combined permeate flow from systems 2 and 3 equals the filtrate flow from system 1, ensuring a constant volume in the suspension tank during the extraction process. The filtration unit is stopped once the protein concentration in the filtrate is below a defined threshold.

The concentration of the OA-filtrate is continued until the protein concentration in the collection tank reaches 20±2 g/L. During this final concentration, the permeate flows to waste. The diafiltration can be performed at the same time as the final concentration.

Process step 1 (continuous extraction and filtration of the protein) has been successfully applied to a continuous extraction system. In order to reduce development costs and maximize IgG recovery, the minimum amount of OA required to precipitate impurities, while reducing the likelihood of IgG loss, must first be determined by laboratory experiments. For this reason, the first concentrate (step 1) was prepared as described in Example 1. The first concentrate obtained from the CE system was used as a starting material for OA Experiments at lab scale.

Example 2

Reduction in Octanoic Acid (OA) for Impurity Removal and IgG Recovery

This example describes the process for determining the minimum amount of OA required to remove impurities from filtered IgG compositions produced according to Process Step 1. Two important criteria for the minimum amount of OA used for precipitation are: 1) achieving a high IgG yield and 2) maintaining a high Quality Attribute (QAT).

Experiment 1

For this experiment Cohn I+II+III paste (2 kg containing 240 gram of Celpure C100) was suspended at a first dilution ratio of 1:6 in 10 mM sodium acetate and 10 mM sodium dihydrogen phosphate dihydrate, pH 4.3-4.4 buffer at 4° C. in the first tank. The suspension in the first tank was stirred at 4° C. with a paddle stirrer for approximately 4 hours. Prior to starting the experiments, the first filtration unit (containing six ceramic filter discs, AD 152 mm with 0.2 µm membranes; filter area=0.216 m$^2$) was stored overnight in cold water (1° C.). At the start of the experiment the water was drained from the unit and the suspension was fed into the unit. The suspension was then recirculated for several minutes between the first tank and the first process unit prior to beginning the filtration process. The ceramic filters in the first process unit were operated at 80 Hz, a rotation speed of 1200 rpm and a feed pressure of 2.2 bar; the over-flow pressure was 0.4-0.8 bar. The permeate from the first process unit was collected in a second tank and then fed into a second unit referred to as the (ultrafiltration/diafiltration) UF/DF unit. The UF/DF unit is a Novoflow dynamic filtration device containing 15 ceramic disks, with 7.0 nm membranes; filter area 0.5 m$^2$. The permeate flow rate of the UF/DF system was 125-180 mL/min. The UF/DF system was started once the first filtrate was collected in the second tank. The retentate of the UF/DF system flows back into the second tank while the permeate flows back into the first tank. The volume of permeate fed back into the first tank contributes to the overall volume of liquid mixed with the paste (i.e. the final dilution factor). In this experiment, the overall recirculation volume was ≥25 L per kg of paste (i.e. 1:25 final dilution factor).

The first concentrate from this experiment has a conductivity of 1.2 mS/cm. The conductivity of the protein solution was adjusted to 8.0 mS/cm with 3.15 M sodium acetate (NaAc) buffer. After LF adjustment, it was no longer necessary to dilute the protein solution.

TABLE 3 shows the results of the first concentrate

| Starting Material | Cohn Fraction I + II + III |
|---|---|
| Precipitate I + II + III amount (kg) | 2 |
| Initial dissolution ratio (Paste + buffer) | 1 + 5 |
| Total protein at initial dissolution ratio (g) | 258.8 |
| Final dissolution ratio (Paste + buffer) | 1 + 24 |

TABLE 3-continued

| shows the results of the first concentrate | |
| --- | --- |
| Starting Material | Cohn Fraction I + II + III |
| Total protein at final dissolution ratio | 284.8 |
| Total weight of first concentrate (kg) | 19 |
| Total process time (h) | 6 |

Experiments 2 to 7

For determination of minimum OA amount required, one kilogram of the first concentrate (from experiment 1) was used for subsequent treatment with different concentrations of OA (0.1; 0.2; 0.25; 0.30; 0.35 to 0.4 g OA/g protein).

The conductivity of the first concentrate was adjusted to 8.0 mS/cm with 3.15 M sodium acetate buffer. The OA addition was carried out with homogenization with Ultraturax (high speed mixer, speed 7000 rpm) for about 5 minutes. The solution was then homogenized for a further 10 minutes with Ultraturax and stirred with a paddle stirrer for 120 minutes. The protein solution was then incubated with 0.6 g calcium phosphate (CAPO) for 30 minutes and 15 minutes with Celpure 100 at 18 g per kilogram solution. Filtration was performed using CH9 filter layers. The subsequent washing was performed using dissolving buffer at 19 to 20% of the starting volume.

Further purification was performed according to the method described in Experiment 8.

Experiment 8

An experiment was performed to compare IgG yield and purity obtained utilizing the CE filtration (Experiments 2 to 7), to the current laboratory process which does not utilize CE filtration. Briefly, the current laboratory process includes OA precipitation of either Precipitate I+II+III or Precipitate A followed by clarifying depth filtration in the presence of filter aid on CH 9 filter sheets and subsequent ultra-/diafiltration and incubation at low pH. In more detail:

The same sample of precipitate (i.e., the starting material from Experiment 1) was used in this experiment, wherein one part of precipitate was re-suspended in buffer. The pH range after re-suspension was 4.8±0.2 pH units.

OA was added to the resuspended precipitate at ~0.12 mol/L and the OA-suspension was further incubated with stirring.

The OA-suspension was subsequently subjected to clarifying depth filtration through a Purafix CH 9 P (Filtrox) filter sheet in the presence of filter aid (0.25 kg Celpure C100/m$^2$ filter area; Advanced Minerals) at pH 4.8.

The solution was diluted to a protein concentration of 20 g/L and the pH was adjusted to approximately pH 4.0 in the presence of polysorbate 80 (P80). The solution was subjected to further clarifying depth filtration.

TABLE 4

| Yield of total protein and IgG following OA precipitation and after incubation at low pH (process intermediate). Results using different OA concentrations are shown. | | | |
| --- | --- | --- | --- |
| Process | g OA/g protein | Protein Yield (g/g paste) | IgG (g/g paste) |
| Experiment 8 | 0.70 | 0.047 | 0.043 |
| Experiment 2 | 0.10 | 0.074 | 0.067 |
| Experiment 3 | 0.20 | 0.070 | 0.064 |
| Experiment 4 | 0.25 | 0.068 | 0.062 |
| Experiment 5 | 0.30 | 0.067 | 0.061 |
| Experiment 6 | 0.35 | 0.055 | 0.050 |
| Experiment 7 | 0.40 | 0.053 | 0.048 |

With decreasing amounts of OA per gram of total protein (in Experiments 2 to 7), the yield of IgG increased compared to yield obtained according to the process of Experiment 8. Therefore, the process of Experiments 2 to 7, which utilizes less OA per gram of protein, provides for a greater yield of IgG as compared to the process of Experiment 8.

Further, the impurity profile of the processes of Experiments 2 to 7 was superior to the impurity profile obtained using Experiment 8.

Details of the amount of impurities such as IgA, IgM and Albumin, protease activity and anti-complement activity as well as QAT parameters such as sub class distribution, molecular size distribution are provided in Table 5, 6, 7 and 8.

TABLE 5

| IgA, IgM and albumin present as impurities following low pH incubation (process intermediate). Results using different OA concentrations are shown. | | | |
| --- | --- | --- | --- |
| Process | g OA/g protein | IgA (g/g paste) | IgM (g/g paste) | Alb. (g/g paste) |
| Experiment 8 | 0.70 | 0.0040 | 0.0018 | <0.0009 |
| Experiment 2 | 0.10 | 0.0068 | 0.0032 | 0.0057 |
| Experiment 3 | 0.20 | 0.0059 | 0.0025 | 0.0040 |
| Experiment 4 | 0.25 | 0.0056 | 0.0015 | 0.0040 |
| Experiment 5 | 0.30 | 0.0051 | 0.0011 | <0.0009 |
| Experiment 6 | 0.35 | 0.0051 | 0.0010 | <0.0010 |
| Experiment 7 | 0.40 | 0.0047 | 0.0010 | <0.0009 |

TABLE 6

| Proteolytic activity and ACA following low pH incubation (process intermediate). Results using different OA concentrations are shown. | | |
| --- | --- | --- |
| Process | g OA/g protein | Proteolytic activity (nkat/g protein) | ACA (%) |
| Experiment 8 | 0.70 | 3 | 20 |
| Experiment 2 | 0.10 | 454 | 15 |
| Experiment 3 | 0.20 | 181 | 13 |
| Experiment 4 | 0.25 | 34 | 8 |
| Experiment 5 | 0.30 | 3 | 7 |
| Experiment 6 | 0.35 | 3 | 4 |
| Experiment 7 | 0.40 | 3 | 7 |

TABLE 7

| | | | | |
|---|---|---|---|---|
| | Gamma-globulin purity. Results using different OA concentrations are shown. | | | |
| Process | g OA/g protein | γ-Globulin [%] | α/β-Globulin [%] | Albumin [%] |
| Experiment 8 | 0.70 | 99.3 | 0.6 | 0.1 |
| Experiment 2 | 0.10 | 90.3 | 2 | 7.7 |
| Experiment 3 | 0.20 | 93.3 | 0.6 | 6.1 |
| Experiment 4 | 0.25 | 91.7 | 0.7 | 7.6 |
| Experiment 5 | 0.30 | 99.4 | 0.3 | 0.3 |
| Experiment 6 | 0.35 | 99.5 | 0.3 | 0.2 |
| Experiment 7 | 0.40 | 99.5 | 0.3 | 0.2 |

TABLE 8

| | | | | |
|---|---|---|---|---|
| | Molecular size distribution, post low pH incubation (process intermediate). Results using different OA concentrations are shown. | | | |
| Process | g OA/g protein | Agg (%) | Dim. (%) | Frag. (%) | Mono. (%) |
| Experiment 8 | 0.70 | 4.5 | 3.7 | <0.1 | 91.7 |
| Experiment 2 | 0.10 | 10.7 | 7.9 | 7.2 | 74.2 |
| Experiment 3 | 0.20 | 4.4 | 7.2 | 4.4 | 84 |
| Experiment 4 | 0.25 | 5 | 9.5 | 1.3 | 84.2 |
| Experiment 5 | 0.30 | 2.8 | 7.4 | <0.1 | 89.7 |
| Experiment 6 | 0.35 | 2.3 | 7.5 | <0.1 | 90.1 |
| Experiment 7 | 0.40 | 2.1 | 6.7 | <0.1 | 91.1 |

Further experiments were performed using a different batch of concentrate obtained according to the method of Experiment 1, and further using reduced OA amounts (0.25, 0.30, 0.35 or 0.40 g of OA) per gram protein and further purification including anion exchange chromatography.

For the following examples the same procedure was used as in Experiments 1 to 8, expanding the further purification of the low pH-incubated solution to include Zeta⁺ filtration and anion exchange chromatography.

Briefly, the additional steps were:

Filter aid is suspended in the intermediate Ig-solution and passed through a Purafix CH 9 P filter sheet combined with subsequent Cuno Z⁺90 LP filtration. The CH 9 filtration in the presence of filter aids represents a depth filtration that has been shown to efficiently remove pathogens such as PRV and picornavirus. The Z⁺ that follows the CH 9 filter is to reduce impurities.

The protein solution is finally filtered inline at a moderately acidic pH through a Pall Ultipor N66 0.1 μm membrane filter, followed by a Pall Ultipor VF FTK DV20 virus filter (a filter capable of removing particles, including viruses as small as approximately 20 nm).

Experiment 9

See above (Experiment 1)

Experiment 10; 11; 12; 13 (see Experiments 2 to 7)

OA concentrations of 0.25; 0.30; 0.35 and 0.40 g OA per gram protein were used, followed by further purification using Zeta+filtration and anion exchange chromatography.

Experiment 14

See Experiment 8

The results of these experiments are provided in Tables 9 to 11:

TABLE 9

| | |
|---|---|
| Results of the first concentrate Experiment 9 | |
| Starting Material | Cohn Fraction I + II + III |
| Precipitate I + II + III amount (kg) | 2 |
| Initial dissolution ratio (Paste + buffer) | 1 + 5 |
| Total protein at initial dissolution ratio (g) | 253 |
| Final dissolution ratio (Paste + buffer) | 1 + 24 |
| Total protein at final dissolution ratio | 267.4 |
| Total weight of first concentrate (kg) | 19 |
| Total process time (h) | 5 |

TABLE 10

| | | | |
|---|---|---|---|
| | Yield of total protein and IgG: Experiments 10 to 14. Results using different OA concentrations are shown. | | |
| Process | g OA/g protein | Protein Yield (g/g paste) | IgG (g/g paste) |
| Experiment 14 | 0.70 | 0.043 | 0.041 |
| Experiment 10 | 0.25 | 0.067 | 0.064 |
| Experiment 11 | 0.30 | 0.063 | 0.060 |
| Experiment 12 | 0.35 | 0.061 | 0.058 |
| Experiment 13 | 0.40 | 0.060 | 0.057 |

As the OA level decreases, the IgG yield increases compared to the current process (Table 10). Important impurities such as IgA, IgM and Albumin, protease activity and anti-complement activity as well as QAT parameters such as sub-class distribution and molecular size distribution are provided in Tables 11, 12, 13 and 14.

TABLE 11

| | | | | |
|---|---|---|---|---|
| | IgA, IgM and albumin as impurities post chromatography. Results using different OA concentrations are shown. | | | |
| Process | g OA/g protein | IgA (g/g paste) | IgM (g/g paste) | Alb. (g/g paste) |
| Experiment 14 | 0.70 | <0.0007 | <0.0006 | <0.0012 |
| Experiment 10 | 0.10 | <0.0009 | <0.0008 | <0.0015 |
| Experiment 11 | 0.20 | <0.0007 | <0.0006 | <0.0012 |
| Experiment 12 | 0.25 | <0.0008 | <0.0007 | <0.0014 |
| Experiment 13 | 0.30 | <0.0007 | <0.0006 | <0.0012 |

TABLE 12

| | | | |
|---|---|---|---|
| | Proteolytic activity and ACA post chromatography. Results using different OA concentrations are shown. | | |
| Process | g OA/g protein | Proteolytic activity (nkat/g protein) | ACA (%) |
| Experiment 14 | 0.70 | 5 | 8 |
| Experiment 10 | 0.25 | 65 | 5 |
| Experiment 11 | 0.30 | 3 | 6 |
| Experiment 12 | 0.35 | 3 | 4 |
| Experiment 13 | 0.40 | 2 | 5 |

TABLE 13

Molecular size distribution, post chromatography.
Results using different OA concentrations are shown.

| Process | g OA/g protein | Agg (%) | Dim. (%) | Frag. (%) | Mono. (%) |
|---|---|---|---|---|---|
| Experiment 14 | 0.70 | <0.1 | 1.5 | <0.1 | 98.3 |
| Experiment 10 | 0.25 | <0.1 | 1.2 | <0.1 | 98.6 |
| Experiment 11 | 0.30 | <0.1 | 1.7 | <0.1 | 98.1 |
| Experiment 12 | 0.35 | <0.1 | 1.7 | <0.1 | 98.1 |
| Experiment 13 | 0.40 | <0.1 | 1.5 | <0.1 | 98.3 |

TABLE 14

Sub-class distribution, post chromatography.
Results using different OA concentrations are shown.

| Process | g OA/g protein | IgG1 (%) | IgG2 (%) | IgG3 (%) | IgG 4 (%) |
|---|---|---|---|---|---|
| Experiment 14 | 0.70 | 74.8 | 22.8 | 0.6 | 1.7 |
| Experiment 10 | 0.25 | 70.1 | 23.9 | 2.4 | 3.2 |
| Experiment 11 | 0.30 | 73.2 | 23.2 | 1.2 | 2.5 |
| Experiment 12 | 0.35 | 74.1 | 23.1 | 0.7 | 2.1 |
| Experiment 13 | 0.40 | 73.7 | 23.7 | 0.6 | 2.1 |

Example 3

Effect of Temperature on Levels of Protease in Purified Product

The precipitate is subjected to purification according to Process 1 and Process 2 as described in Example 1. Briefly, the starting material (Precipitate I+II+III or Precipitate A) is resuspended in the resuspension buffer (1:5) using an impeller mixer, at a temperature between 18-22° C., and then transferred to the suspension tank.

The suspension is pumped to the first processing unit to start the continuous extraction process. The unfiltered suspension returns to the suspension tank as retentate. This circulation is maintained while solubilized proteins are filtered across the ceramic discs. The filtrate containing IgG is collected in a second tank (filtrate tank). When a defined volume in the second tank (filtrate tank) is reached, the concentration process is started using ultrafiltration and diafiltration membranes (systems 2 and 3). The transmembrane pressure (TMP) is regulated to ensure that the combined permeate flow from systems 2 and 3 is slightly higher than the filtrate flow from system 1, ensuring a constant volume in the suspension tank during the extraction process. The permeate is also used for filling the backflush tank. The filtration unit is stopped once the protein concentration in the filtrate is below a defined threshold.

The first concentrate, (filtrate/concentrate) is adjusted to total protein concentration of between about 15-18 g/L). If necessary, the conductivity of this concentrate is adjusted to (8±1 mS/cm), with pH in the range of about 4.75 to about 4.85.

The adjusted concentrate is then transferred to a tank for precipitation with octanoic acid (OA). This can be the same tank used for suspension of the starting material (i.e., the suspension tank) but after the tank has been cleaned.

OA addition and incubation were performed at different temperatures in a series of experiments e.g. 22° C., 27° C., 32° C. and higher. The duration of OA addition, mixing intensity and all other parameters were kept constant, in order to study the temperature effect on the reduction of protease activity.

After addition of the OA amount the OA-suspension is recirculated over the system (1) in order to enable dispersion of OA and extraction of IgG.

The OA-suspension is pumped to the first processing unit to start the continuous extraction-filtration process. The unfiltered suspension returns to the suspension tank as retentate. This circulation is maintained while IgG and other globulins are filtered across the ceramic discs. The OA-filtrate is collected in a second tank. When a defined volume in the second tank (filtrate tank) is reached, the concentration process is started using systems 2 and 3. The concentration step can also be started immediately if systems 2 and 3 are filled with buffer.

The transmembrane pressure (TMP) is regulated to ensure that the combined permeate flow from systems 2 and 3 is slightly higher than the filtrate flow from system 1, ensuring a constant volume in the suspension tank during the extraction process.

The flow rate of the combined permeate from systems 2 and 3 is slightly higher than the filtrate flow from system 1, which facilitates the use of this permeate as backflush buffer.

The filtration unit is stopped once the protein concentration in the filtrate is below a defined threshold.

The concentration of the OA-filtrate is continued until the protein concentration in the collection tank reaches 20±2 g/L. During this final concentration, the permeate flows to waste. Diafiltration can be done at the same time during final concentration.

The concentration and degree of protease activity in the final concentrate was determined using standard methods. Briefly, serine protease activity was measured by the ability of protein concentrate to cleave the chromogenic substrate Ile-Pro-Arg-pNA (S-2288). During this reaction p-Nitroanilin (pNA) is released which is measured in a photometer at 405 nm. Serine protease activity was measured in conditions where the pH was 8.4 at 37° C. Kallikrein-like activity was measured by cleavage of the chromogenic substrate H-D-Pro-Phe-Arg-pNA (S-2302). During this reaction p-Nitroanilin (pNA) is released which is measured in a kinetic mode by a photometer at 405 nm.

Quantitative assessment of IgA, IgM and IgG subclasses were determined using standard techniques.

Results

As summarized in the below Tables 15 and 17, the results indicate that incubation of the OA-suspension at a temperature of greater than 22° C., preferably in the range of 25° C. to 37° C., preferably 25° C. to 32° C. or 27° C. to 32° C., most preferably about 32° C., reduces the amount of protease present in the final protein preparation. Tables 16 and 18 confirm the high level of recovery of Ig and subclasses at all temperatures tested.

TABLE 15

Impact of temperature on protease impurity as measured following OA precipitation, filtration and UF/DF. Starting material Precipitate A.

| Octanoic acid incubation temperature (° C.) | Pre-kallikrein activator (PA) (nkat/L) | Kallikrein (KK) (ng/mL) |
|---|---|---|
| 27 | 476 | 255 |
| 37 | 105 | 75 |

43

TABLE 16

| Starting material Precipitate A | | | | |
| --- | --- | --- | --- | --- |
| | Octanoic acid incubation temperature (° C.) | | | |
| | 22° C. | 27° C. | 32° C. | 37° C. |
| IgA (ELISA) mg/L | 747.46 | 1015.25 | 739.48 | 854 |
| IgA (Nephelometric) mg/L | 700 | 700 | 740 | 1100 |
| IgM (ELISA) mg/L | 1031 | 1308.74 | 868.1 | 1244.8 |
| IgM (Nephelometric) mg/L | 1010 | 1130 | 1043.8 | 1153 |
| IgG subclasses (%) IgG1 | 69.3 | 62.7 | 64.9 | 62.6 |
| IgG2 | 25.3 | 30.4 | 28.12 | 29 |
| IgG3 | 1 | 0.9 | 1.44 | 2.15 |
| IgG4 | 4.4 | 6 | 5.56 | 6.25 |

TABLE 17

| Impact of temperature on protease impurity as measured following OA precipitation, filtration and UF/DF. Starting material Fraction I + II + III | | |
| --- | --- | --- |
| Octanoic acid incubation temperature (° C.) | Pre-kallikrein activator (PA) (nkat/L) | Kallikrein (KK) (ng/mL) |
| 20 | 873 | 276 |
| 32 | 65 | <3.9 |
| 37 | 56 | <3.9 |

TABLE 18

| Starting material Fraction I + II + III | | | | | |
| --- | --- | --- | --- | --- | --- |
| | Octanoic acid incubation temperature (° C.) | | | | |
| | 20° C. | 22° C. | 27° C. | 32° C. | 37° C. |
| IgA (ELISA) mg/L | 1490 | 1225.7 | 1044 | 1072 | 1054 |
| IgA (Nephelometric) mg/L | 1400 | 1200 | 1150 | 1080 | 966 |
| IqM (ELISA) mq/L | 882.45 | 737.26 | 660 | 649 | 797 |
| IqM (Nephelometric) mq/L | 746 | 651 | 290 | 628.8 | 657 |
| IgG subclasses (%) IgG1 | 69.1 | 69.9 | 70.7 | 71.52 | 74.8 |
| IgG2 | 22.1 | 22.2 | 21.45 | 22.5 | 19.9 |
| IgG3 | 3.5 | 3.2 | 2.7 | 1.54 | 1.3 |
| IgG4 | 5.3 | 4.8 | 5.2 | 4.34 | 3.97 |

It will be understood that the invention disclosed and defined in this specification extends to all alternative combinations of two or more of the individual features mentioned or evident from the text or drawings. All of these different combinations constitute various alternative aspects of the invention.

The invention claimed is:

1. An industrial scale method for extracting a protein of interest in high yield from a precipitate, comprising:

a) mixing the precipitate with a liquid in a first tank to form a first suspension having a first dilution factor;

b) feeding the first suspension into a first filtration unit comprising a rotational cross flow filter element comprising a filter disc having a ceramic membrane with an average pore size from 5 nm to 5000 nm, the filter element adapted to produce (i) a first retentate depleted of the protein of interest and (ii) a first permeate enriched with the protein of interest;

c) diluting the first suspension in the first tank by adding liquid to a second dilution factor in part by streaming the first retentate into the first tank;

d) recovering the first permeate enriched with the protein of interest in a second tank; and

e) subjecting the first permeate in the second tank to a continuous concentration process in a second filtration unit comprising a cross flow filter element, thereby producing a second retentate enriched with the protein of interest and a second permeate depleted of the protein of interest;

f) optionally diluting the first suspension in the first tank by continuously streaming the second permeate to the first tank, thereby diluting the suspension to the second dilution factor; and g) one or both of (i) returning the second retentate enriched with the protein of interest to the second tank and (ii) collecting the second retentate enriched with the protein of interest;

h) precipitating one or more impurities in the second retentate enriched with the protein of interest to produce a second suspension; and i) removing the precipitated impurities from the second suspension to produce a solution containing the protein of interest.

2. The method of claim 1, further comprising removing the precipitated impurities from the second suspension by feeding the second suspension into a third filtration unit comprising a dynamic filter element adapted to produce a third retentate containing the one or more precipitated impurities and a third permeate enriched with the protein of interest; optionally further comprising streaming the third retentate into the tank comprising the second suspension; optionally further comprising recovering the third filtrate enriched with the protein of interest in a further tank.

3. The method of claim 2, wherein removing the precipitated impurities from the second suspension further comprises subjecting the third permeate in the further tank to a continuous concentration process in a fourth filtration unit comprising a cross flow filter element, thereby producing a fourth retentate enriched with the protein of interest and a fourth permeate depleted of the protein of interest; wherein the method optionally further comprises diluting the suspension in the tank comprising the second suspension by streaming the fourth permeate to the tank comprising the second suspension, thereby diluting the suspension to a third dilution factor; and optionally one or both of (i) returning the fourth retentate enriched with the protein of interest to the further tank and (ii) collecting the fourth retentate enriched with the protein of interest.

4. The method of claim 1, wherein the first retentate and the second permeate are continuously streamed into the first tank to dilute the suspension to the second dilution factor.

5. The method of claim 1, wherein the filtration unit adapted to produce a permeate enriched for the protein of interest comprises more than one hollow shaft adapted to collect the permeate, each shaft connected to at least one filter disc comprising a ceramic membrane.

6. The method of claim 1, wherein the filtration unit for performing the concentration process comprises a dynamic cross flow filter element.

7. The method of claim 1, wherein the second suspension comprises a solvent and precipitating the one or more impurities from the permeate or retentate enriched with the protein of interest is by comprises altering a solvation potential of the solvent.

8. The method of claim 7, wherein altering the solvation potential of the solvent comprises lowering the solubility of the one or more impurities by one or both of adding a reagent and modulating a pH or conductivity of the second suspension.

9. The method of claim 8, wherein the reagent for precipitating the one or more impurities is an ionizable organic additive.

10. The method of claim 9, wherein the ionizable organic additive is a fatty acid, or a salt or ester thereof.

11. The method of claim 10, wherein the fatty acid is selected from enanthic (heptanoic) acid, caprylic (octanoic) acid, octenoic acid, pelargonic (nonanoic) acid, nonenoic acid, or capric (decanoic) acid, and salts and esters thereof.

12. The method of claim 8, wherein the reagent for precipitating the one or more impurities from the permeate or retentate enriched with the protein of interest is a nonionic organic polymer.

13. The method of claim 12, wherein the non-ionic organic polymer is selected from polyethylene glycol (PEG), polypropylene glycol, polyvinylpyrrolidone, dextran, and cellulose.

14. The method of claim 1, wherein the precipitate comprising the protein of interest is an intermediate product of an alcohol fractionation process of human blood plasma.

15. The method of claim 14, wherein the intermediate product is a plasma fraction selected from the group consisting of Cohn Fraction I (Fr I), Cohn Fraction II+III (Fr II+III), Cohn Fraction I+II+III (Fr I+II+III), Cohn Fraction II (Fr II), Cohn Fraction III (Fr III), Cohn Fraction IV (Fr IV), Cohn Fraction V (Fr V), Kistler/Nitschmann Precipitate A (KN A), Kistler/Nitschmann Precipitate B (KN B), Kistler/Nitschmann Precipitate C (KN C), and combinations of one or more thereof.

16. The method of claim 1, wherein the protein-comprising precipitate is obtained from a culture supernatant, a fermentation product or a material derived from a milk or whey fraction.

17. The method of claim 1, wherein the protein of interest is an immunoglobulin.

18. The method of claim 1 wherein the first suspension is continuously fed into the first filtration unit until the first suspension has been diluted to at least the second dilution factor.

19. The method of claim 1, wherein the method comprises periodic backflushing intervals, wherein flow of liquid through the filtration units is reversed at regular intervals and for a defined period of time.

20. The method of claim 1, wherein the method recovers at least 75%, of the protein of interest in the protein-comprising precipitate.

\* \* \* \* \*